US008180460B2

(12) United States Patent
Nevsmith et al.

(10) Patent No.: US 8,180,460 B2
(45) Date of Patent: May 15, 2012

(54) FLEXIBLE CIRCUIT ELECTRODE ARRAY

(75) Inventors: Jordan Matthew Nevsmith, Pasadena, CA (US); Neil Hamilton Talbot, La Crescenta, CA (US); James Singleton Little, Saugus, CA (US); Brian V. Mech, Stevenson Ranch, CA (US); Robert J. Greenberg, Los Angeles, CA (US); Qingfang Yao, Valencia, CA (US); Dao Min Zhou, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 496 days.

(21) Appl. No.: 11/934,627

(22) Filed: Nov. 2, 2007

(65) Prior Publication Data

US 2008/0288037 A1   Nov. 20, 2008

Related U.S. Application Data

(63) Continuation-in-part of application No. 11/821,328, filed on Jun. 21, 2007, now Pat. No. 7,991,478, which is a continuation-in-part of application No. 11/413,689, filed on Apr. 28, 2006, which is a continuation-in-part of application No. 11/207,644, filed on Aug. 19, 2005, now Pat. No. 8,014,878.

(60) Provisional application No. 60/856,455, filed on Nov. 2, 2006, provisional application No. 60/815,311, filed on Jun. 21, 2006, provisional application No. 60/676,008, filed on Apr. 28, 2005.

(51) Int. Cl.
*A61N 1/05* (2006.01)

(52) U.S. Cl. ............... 607/116

(58) Field of Classification Search ............... 607/116, 607/53–54
See application file for complete search history.

(56) References Cited

U.S. PATENT DOCUMENTS

| 5,109,844 | A |   | 5/1992  | de Juan, Jr. et al. |
|-----------|---|---|---------|---------------------|
| 5,505,201 | A | * | 4/1996  | Grill et al. ............ 600/371 |
| 5,575,813 | A |   | 11/1996 | Edell et al.        |
| 5,935,155 | A |   | 8/1999  | Humayun et al.      |
| 5,944,747 | A |   | 8/1999  | Greenberg et al.    |
| 6,374,143 | B1|   | 4/2002  | Berrang et al.      |
| 6,400,989 | B1|   | 6/2002  | Eckmiller           |
| 6,458,157 | B1|   | 10/2002 | Suaning             |

(Continued)

OTHER PUBLICATIONS

Shamma-Donoghue, et al., Thin-Film Multielectrode Arrays for a Cochlear Prosthesis; IEEE Trans. Elec. Dev., vol. Ed-29, No. 1, Jan. 1982.

*Primary Examiner* — Scott Getzow
*Assistant Examiner* — Amanda Patton
(74) *Attorney, Agent, or Firm* — Scott B. Dunbar; Gary Schnittgrund

(57) ABSTRACT

A flexible circuit electrode array with more than one layer of metal traces comprising: a polymer base layer; more than one layer of metal traces, separated by polymer layers, deposited on said polymer base layer, including electrodes suitable to stimulate neural tissue; and a polymer top layer deposited on said polymer base layer and said metal traces. Polymer materials are useful as electrode array bodies for neural stimulation. They are particularly useful for retinal stimulation to create artificial vision, cochlear stimulation to create artificial hearing, or cortical stimulation many purposes. The pressure applied against the retina, or other neural tissue, by an electrode array is critical. Too little pressure causes increased electrical resistance, along with electric field dispersion. Too much pressure may block blood flow.

15 Claims, 24 Drawing Sheets

U.S. PATENT DOCUMENTS

| | | |
|---|---|---|
| 6,516,228 B1 | 2/2003 | Berrang et al. |
| 6,843,870 B1 | 1/2005 | Bluger |
| 2002/0091421 A1 | 7/2002 | Greenberg et al. |
| 2002/0111658 A1 | 8/2002 | Greenberg et al. |
| 2003/0233134 A1* | 12/2003 | Greenberg et al. ............ 607/36 |

* cited by examiner

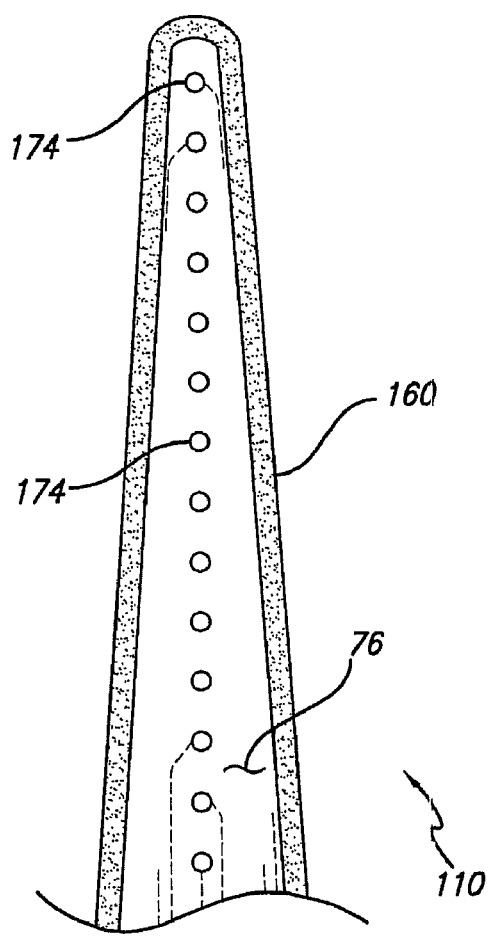
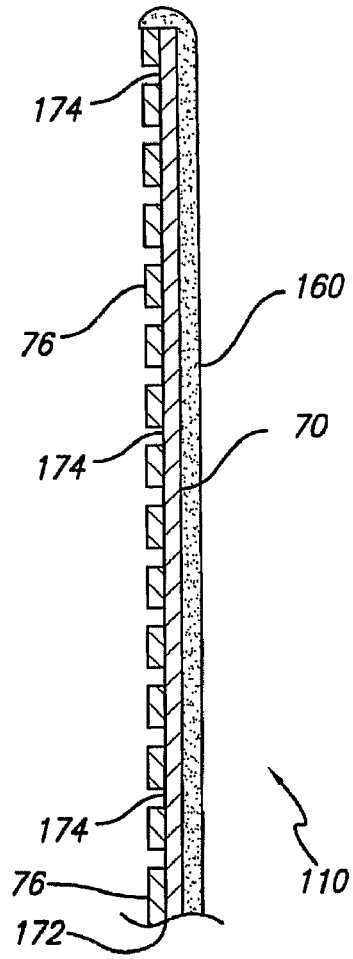
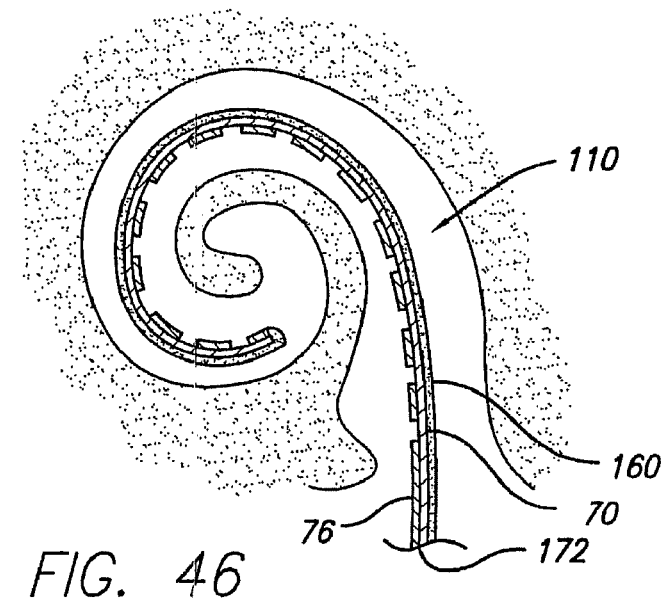

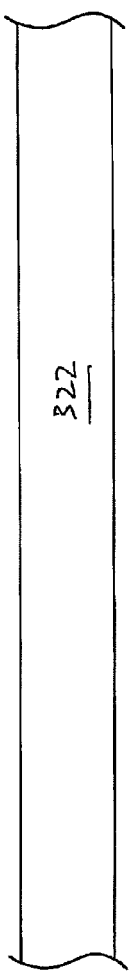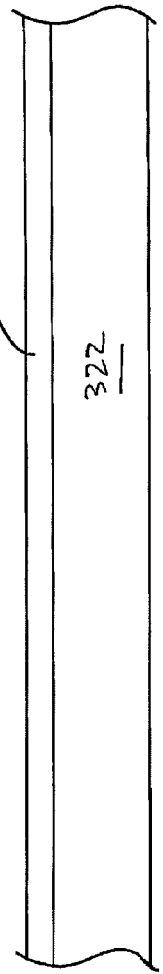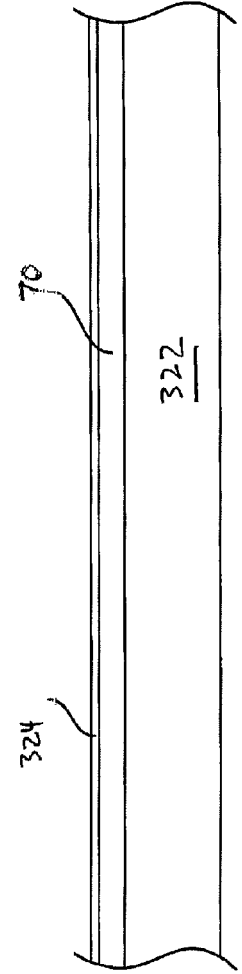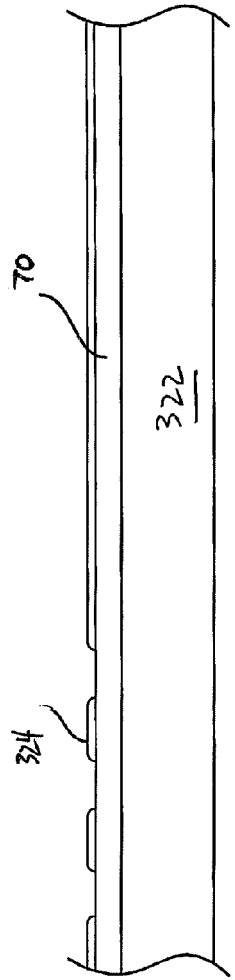

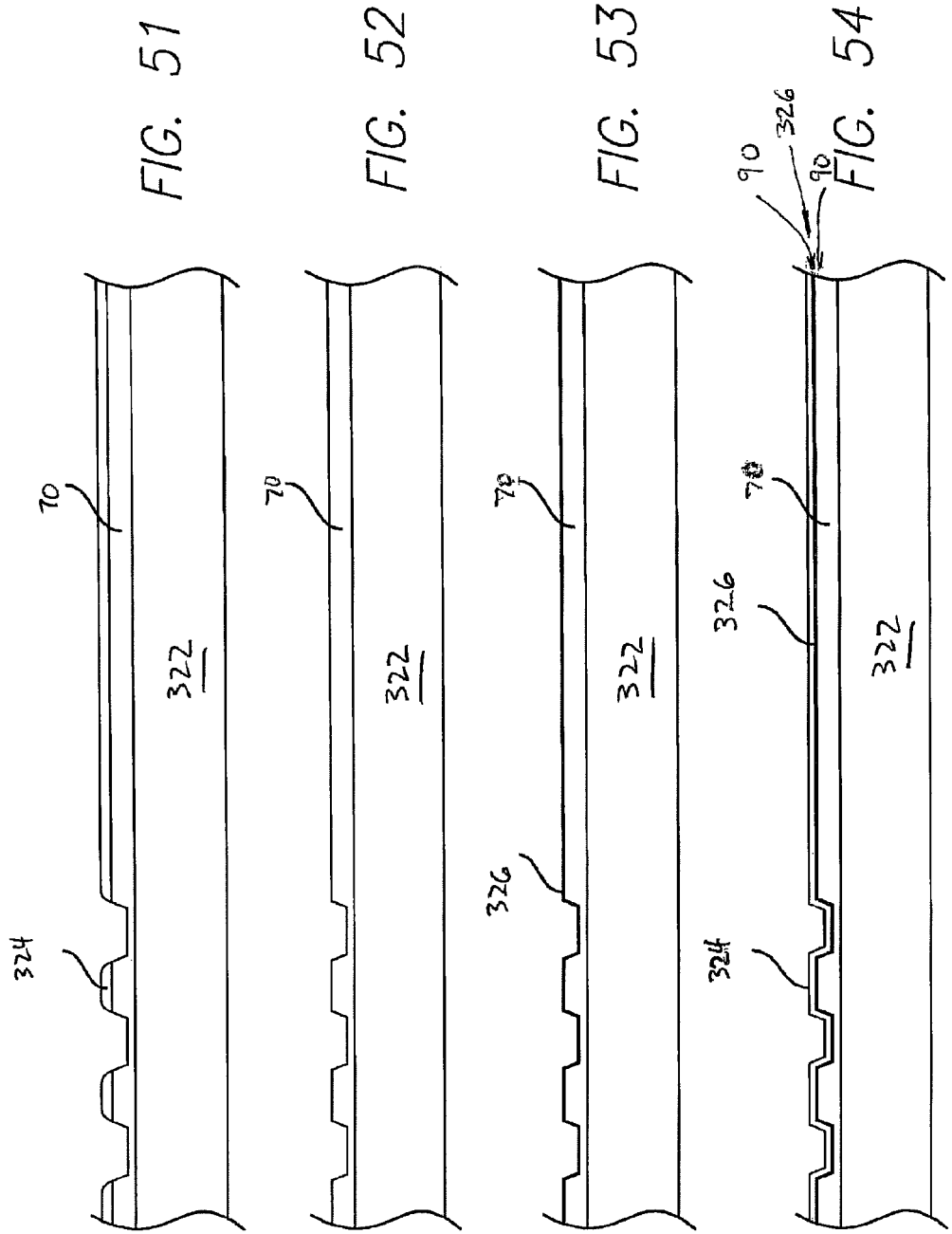

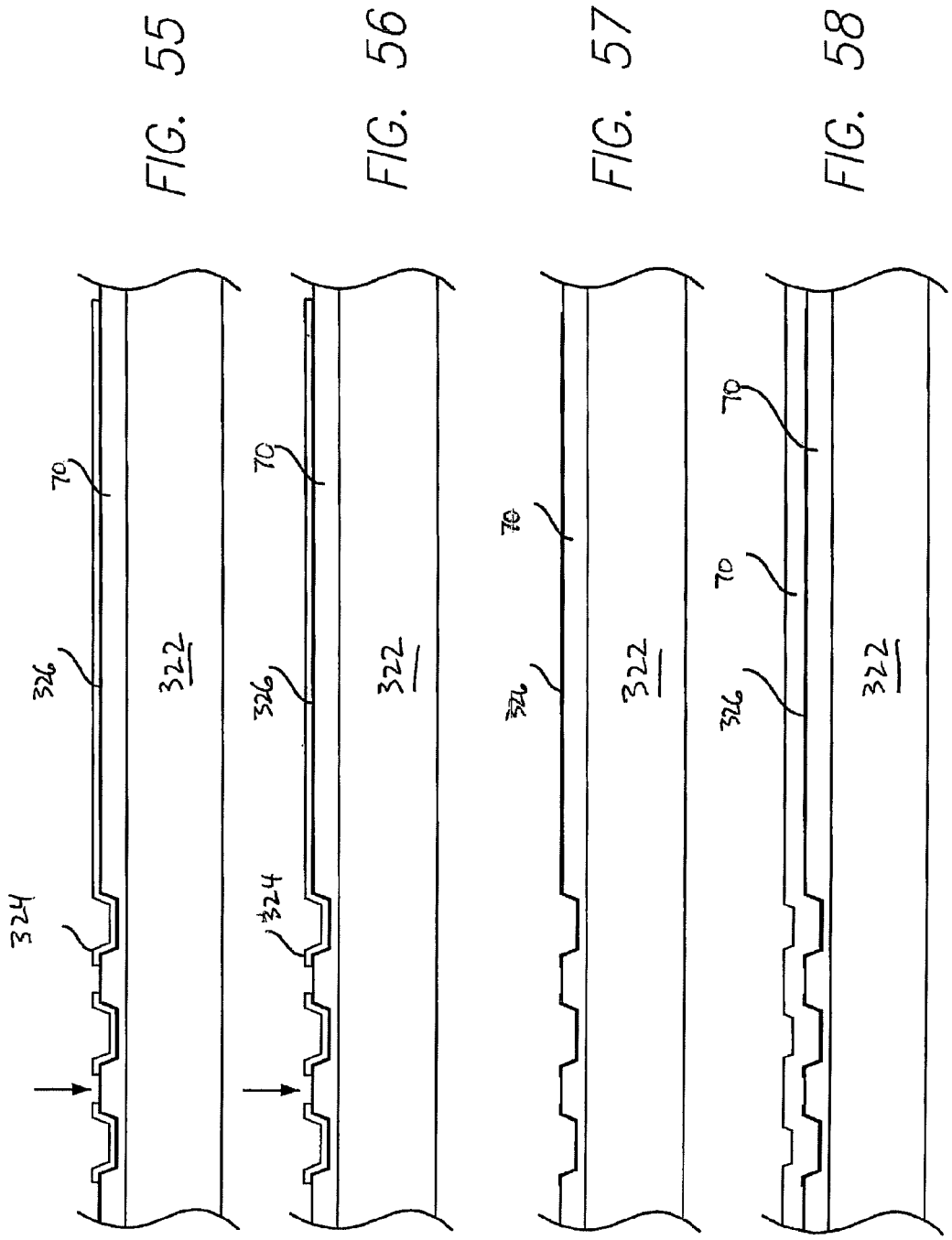

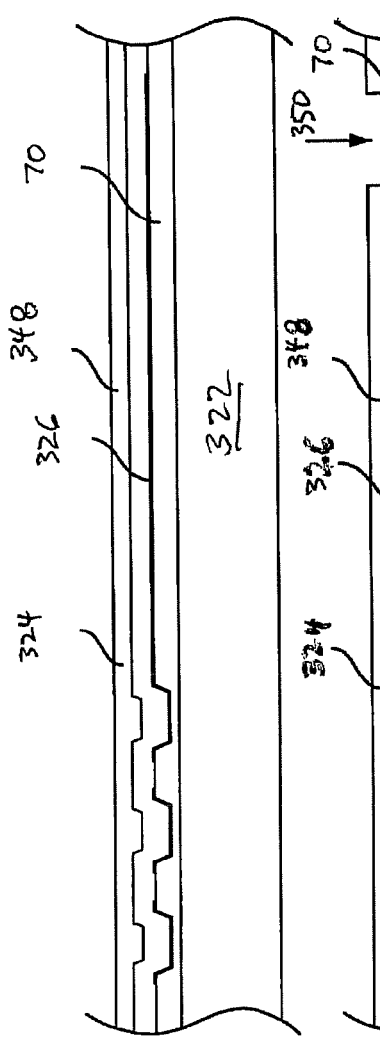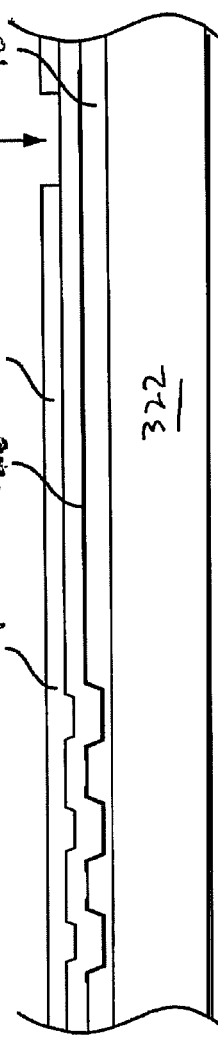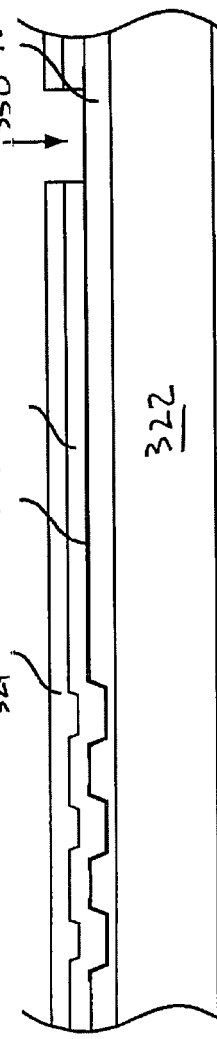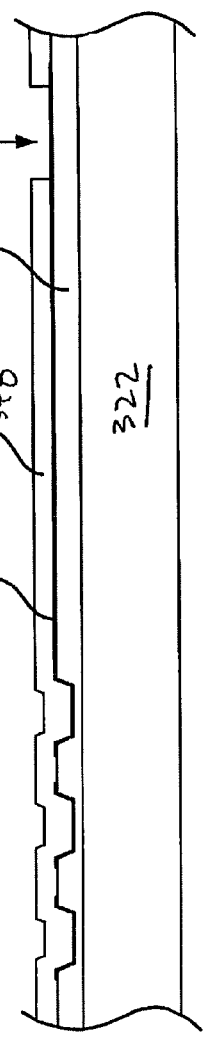

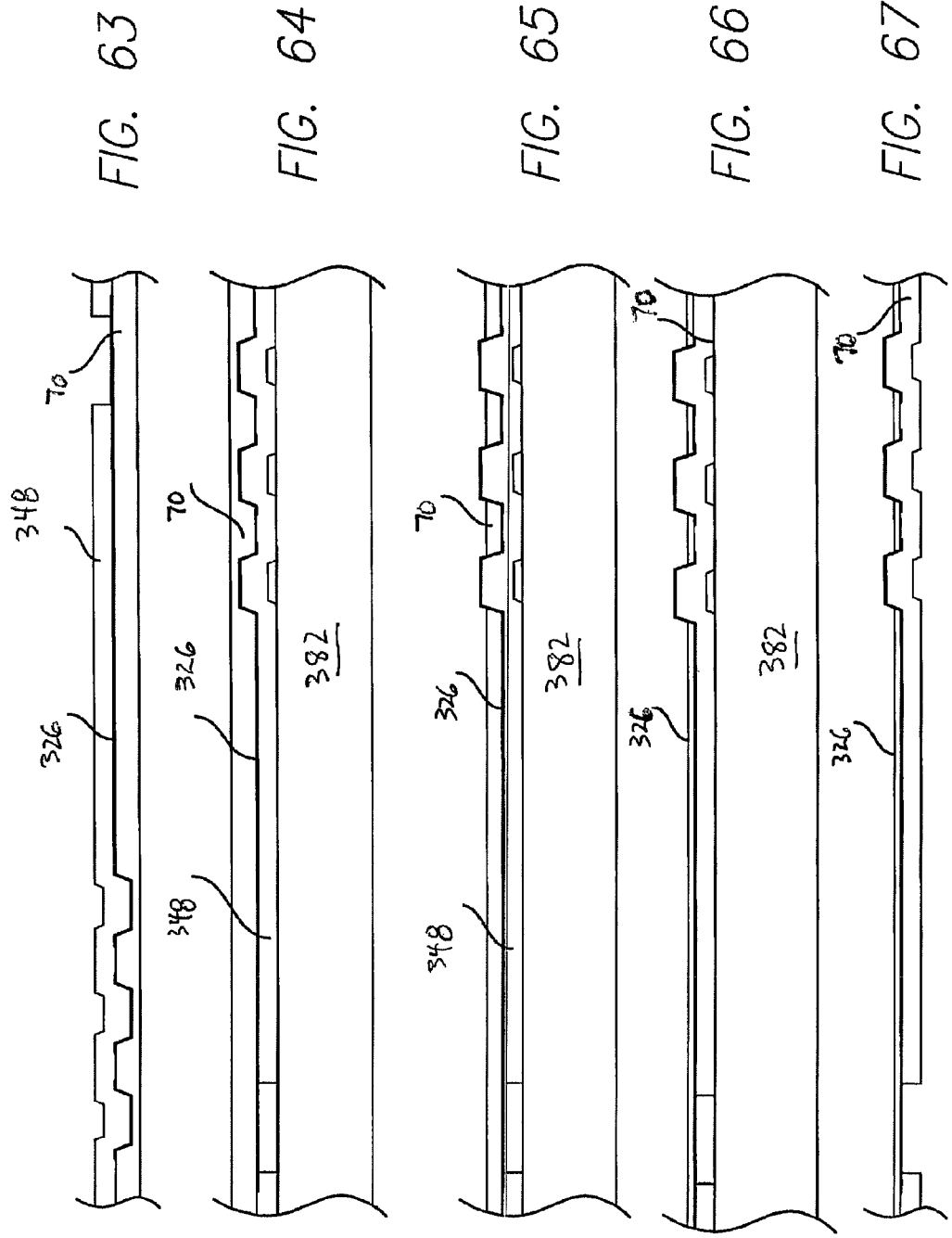

FLEXIBLE CIRCUIT ELECTRODE ARRAY

CROSS-REFERENCE TO RELATED APPLICATIONS

This application claims the benefit of U.S. Provisional Application No. 60/856,455, "Flexible Circuit Electrode Array", filed Nov. 2, 2006.

This application is a Continuation-In-Part of U.S. application Ser. No. 11/821,328, filed Jun. 21, 2007, now U.S. Pat. No. 7,991,478, "Flexible Circuit Electrode Array with At Least One Track Opening," published as US 2007/0265665 on Nov. 15, 2007, which claims the benefit of U.S. Provisional Application No. 60/815,311, filed Jun. 21, 2006, "Flexible Circuit Electrode Array with at Least One Tack Opening."

U.S. application Ser. No. 11/821,328 is a Continuation-In-Part of U.S. application Ser. No. 11/413,689, filed Apr. 28, 2006, "Flexible Circuit Electrode Array," published as US 2006/0259112 on Nov. 16, 2006, which is a Continuation-In-Part of U.S. application Ser. No. 11/207,644, filed Aug. 19, 2005, now U.S. Pat. No. 8,014,878, "Flexible Circuit Electrode Array," published as US 2006/0247754 on Nov. 2, 2006, which claims the benefit of U.S. Provisional Application No. 60/676,008, filed Apr. 28, 2005, "Thin Film Electrode Array", all of which are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for neural stimulation.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

One aspect of the disclosure is a flexible circuit electrode array with more than one layer of metal traces comprising: a polymer base layer; more than one layer of metal traces, separated by polymer layers, deposited on said polymer base layer, including electrodes suitable to stimulate neural tissue; and a polymer top layer deposited on said polymer base layer and said metal traces.

The novel features of the invention are set forth with particularity in the appended claims. The invention will be best understood from the following description when read in conjunction with the accompanying drawings.

BRIEF DESCRIPTION OF THE DRAWINGS

FIG. 44 shows of front view of a cochlear electrode array according to the present invention.

FIG. 45 shows a side view of a cochlear electrode array according to the present invention.

FIG. 46 shows a cochlear electrode array according to the present invention as implanted in the cochlea.

FIG. 47 to FIG. 67 depicts the sequence of a new process for producing a flexible circuit electrode array.

FIG. 47 depicts a cross-sectional view of substrate, comprising glass or silicon.

FIG. 48 depicts a cross-sectional view of the substrate and a layer of polymer deposited on the substrate.

FIG. 49 depicts a cross-sectional view of the substrate with photoresist deposited on the polymer.

FIG. 50 depicts a cross-sectional view of the layer structure and photoresist after being exposed and developed.

FIG. 51 depicts a cross-sectional view of the layer structure after polymer etching.

FIG. 52 depicts a cross-sectional view of the layer structure after stripping the photoresist.

FIG. 53 depicts a cross-sectional view of the layer structure after depositing thin film metals.

FIG. 54 depicts a cross-sectional view of the layer structure after depositing a photoresist layer on the thin film.

FIG. 55 depicts a cross-sectional view of the layer structure and photoresist after being exposed and developed.

FIG. 56 depicts a cross-sectional view of the layer structure after etching the thin film metal layer.

FIG. 57 depicts a cross-sectional view of the layer structure after stripping the photoresist.

FIG. 58 depicts a cross-sectional view of the layer structure after applying a top polymer layer.

FIG. 59 depicts a cross-sectional view of the layer structure after applying a photoresist layer on the top polymer layer.

FIG. 60 depicts a cross-sectional view of the layer structure and photoresist after being exposed and developed.

FIG. 61 depicts a cross-sectional view of the layer structure after etching the top polymer layer.

FIG. 62 depicts a cross-sectional view of the layer structure after stripping the photoresist.

FIG. 63 depicts a cross-sectional view of the layer structure after releasing the structure from the substrate.

FIG. 64 depicts a cross-sectional view of the layer structure turned upside down and applied on a new substrate.

FIG. 65 depicts a cross-sectional view of the layer structure after etching down the polymer layer to the metal layer.

FIG. 66 depicts a cross-sectional view of the layer structure with deeper etching of the polymer to obtain protruding contacts FIG. 67 depicts a cross-sectional view of the layer structure after releasing the structure from the substrate.

DETAILED DESCRIPTION OF THE PREFERRED EMBODIMENTS

The following description is the best mode presently contemplated for carrying out the invention. This description is not to be taken in a limiting sense, but is made merely for the purpose of describing the general principles of the invention. The scope of the invention should be determined with reference to the claims.

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating or casting. A layer of metal, preferably platinum, is applied to the polymer and patterned to create electrodes and leads for those electrodes. Patterning is commonly done by photolithographic methods. A polymer second layer 75 is applied over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

The pressure applied against the retina, or other neural tissue, by an electrode array is critical. Too little pressure causes increased electrical resistance between the array and retina, along with electric field dispersion. Too much pressure may block blood flow causing retinal ischemia and hemorrhage. Pressure on the neural retina may also block axonal flow or cause neuronal atrophy leading to optic atrophy. Common flexible circuit fabrication techniques such as photolithography generally require that a flexible circuit electrode array 10 be made flat. Since the retina is spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

It is further advantageous to provide a fold or twist in the flexible circuit electrode array 10 at the point where it passes through the sclera. Additional material may be added inside and outside the fold to promote a good seal with the scleral tissue.

Figure 1:
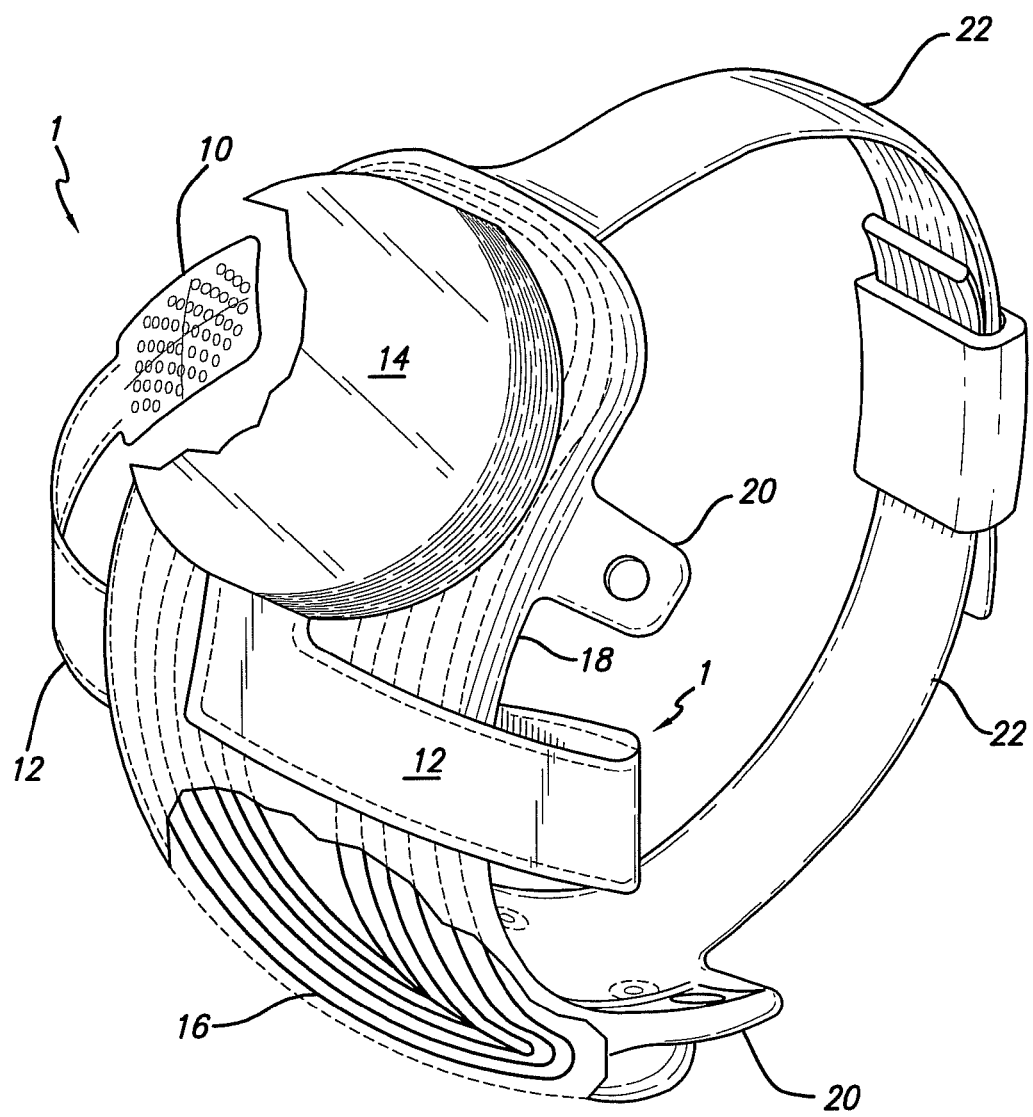
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
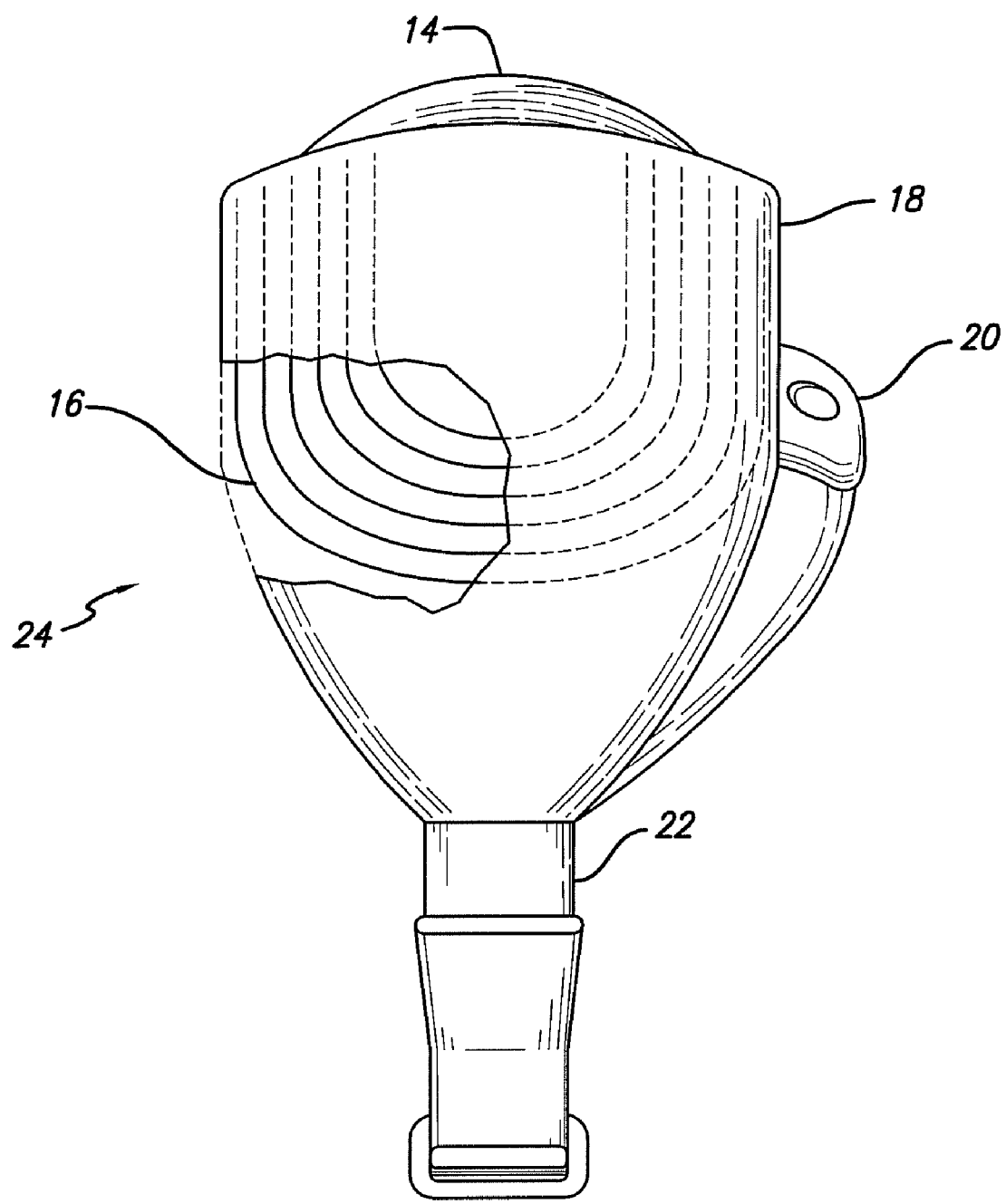
FIG. 2 is a side view of the implanted portion of the preferred retinal prosthesis showing the fan tail in more detail.
Figure 3A:
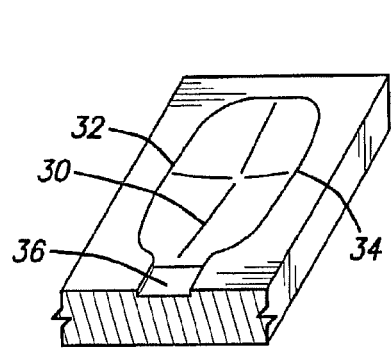
FIG. 3A-3 E depict molds for forming the flexible circuit array in a curve.
Figure 3B:
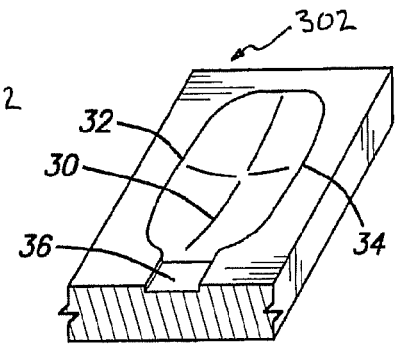
Figure 3C:
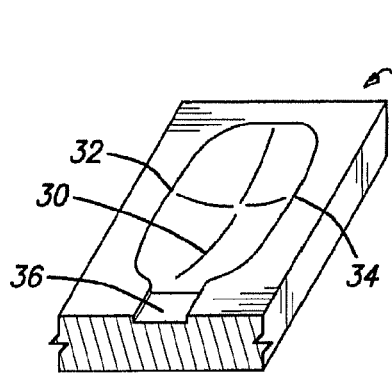
Figure 3D:
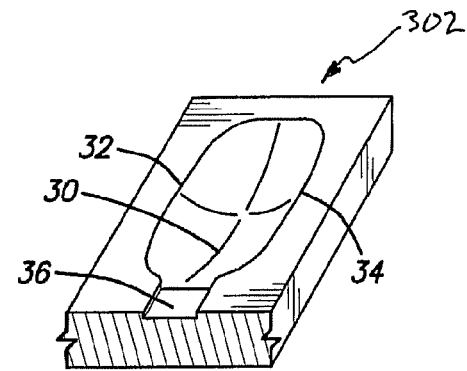
Figure 3E:
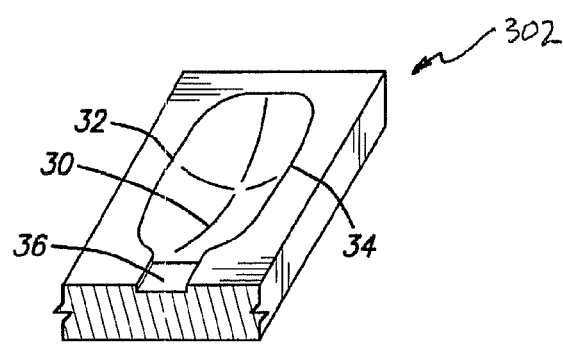

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrodes 74 and bond pad 52 to improve electrical continuity. This can be accomplished through any of the above methods or electroplating. Then, the top polymer layer 76 is applied over the metal. Openings in the top polymer layer 76 for electrical contact to the electronics package 14 and the electrodes 74 may be accomplished by laser ablation, reactive ion etching (RIE), or photolithograph and wet etch. Making the electrode openings in the top polymer layer 76 smaller than the electrodes 74 promotes adhesion by avoiding delaminating around the electrode edges.

The pressure applied against the retina by the flexible circuit electrode array 10 is critical. Too little pressure causes increased electrical resistance between the flexible circuit electrode array 10 and retina. It should be noted that while the present invention is described in terms of application to the retina, the techniques described are equally applicable to many forms of neural stimulation. Application to the retina requires a convex spherical curve. Application to the cochlea requires a constant curve in one dimension and a spiral curve in the other dimension. Application to the cerebral cortex requires a concave spherical curve. Cortical stimulation is useful for artificial vision or hearing, touch and motor control for limb prostheses, deep brain stimulation for Parkinson's disease and multiple sclerosis and many other applications.

Common flexible circuit fabrication techniques such as photolithography generally require that a flexible circuit electrode array 10 be made flat. Since the retina is spherical, a flat array will necessarily apply more pressure near its edges, than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIG. 3 illustrates a series of molds 302 according to the preferred embodiment. Since the flexible circuit electrode array 10 will maintain a constant length, the curvature is slowly increased along that length. As the curvature 30 decreases in successive molds (FIGS. 3A-3E) the straight line length between ends 32 and 34 decreases to keep the length along the curvature 30 constant, where the mold 302, FIG. 3E, approximates the curvature of the retina or other desired neural tissue. The molds 302 provide a further opening 36 for the flexible circuit cable 12 of the flexible circuit electrode array 10 to exit the mold 302 without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array and the retina. Hence, the amount of curvature is a compromise between the desired curvature, array surface area, and the properties of the material.

Figure 4:
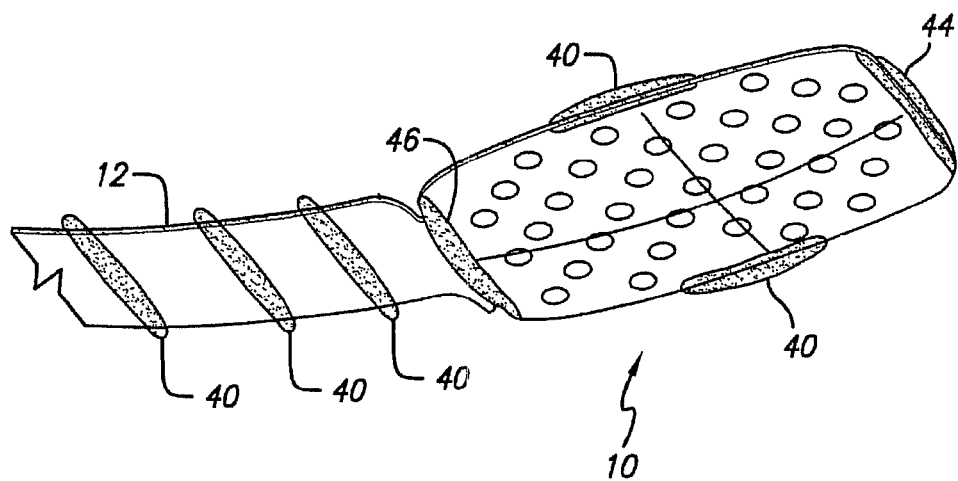
FIG. 4 depicts an alternate view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array to round the edges and protect the retina. Silicone around the entire edge may make the flexible circuit less flexible. So, it is advantageous to provide silicone bumpers or ribs to hold the edge of the flexible circuit electrode array away from the retinal tissue. Curvature 40 fits against the retina. The leading edge 44 is most likely to cause damage and is therefore fitted with molded silicone bumper. Also, edge 46, where the array lifts off the retina, can cause damage and should be fitted with a bumper. Any space along the side edges of curvature 40 may cause damage and may be fitted with bumpers as well. It is also possible for the flexible circuit cable 12 of the electrode array to contact the retina. It is, therefore, advantageous to add periodic bumpers along the flexible circuit cable 12.

It is also advantageous to create a reverse curve or service loop in the flexible circuit cable 12 of the flexible circuit electrode array 10 to gently lift the flexible circuit cable 12 off the retina and curve it away from the retina, before it pierces the sclera at a sclerotomy. It is not necessary to heat curve the service loop as described above, the flexible circuit electrode array 10 can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array 10 must be inside the sclera in order to contact the retina. The sclera is cut through at the pars plana, forming a sclerotomy, and the flexible circuit passed through the sclerotomy. A flexible circuit is thin but wide. The more electrode wires, the wider the flexible circuit must be. It may be difficult to seal a sclerotomy over a flexible circuit electrode array 10 that is wide enough to support enough wires for a high resolution array. A narrow sclerotomy is preferable.

Figure 5:
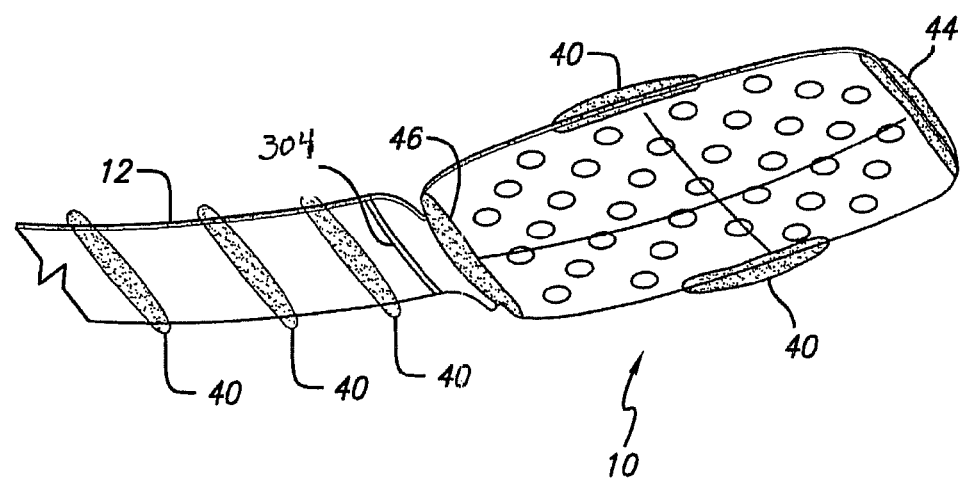
FIG. 5 depicts an alternate view of the invention with ribs to help maintain curvature and prevent retinal damage fold of the flexible circuit cable and a fold A between the circuit electrode array and the flexible circuit cable.

FIG. 5 depicts a further embodiment of the part of the prosthesis shown in FIG. 4 with a fold 304 between the circuit electrode array 10 and the flexible circuit cable 12. The angle in the fold 304, also called ankle, has an angle of 1°-180°, preferably 80°-120°. The fold 304 is advantageous since it reduces tension and enables an effective attachment of the flexible electrode circuit array 10 to the retina.

Figure 6:
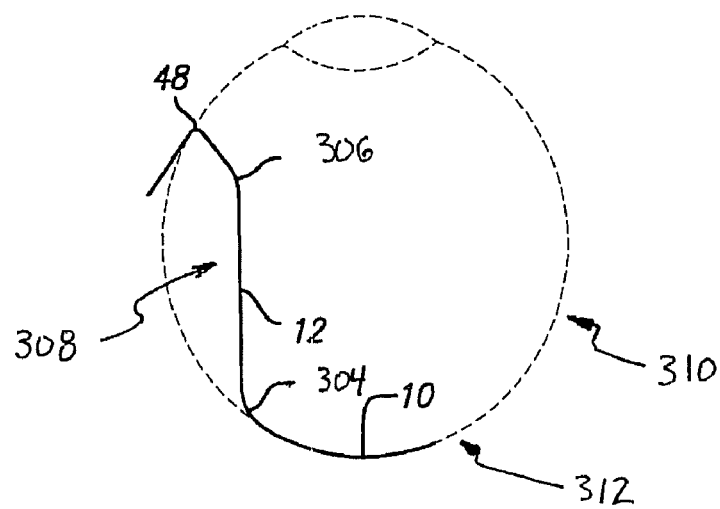
FIG. 6 depicts a cross-sectional view of the prosthesis shown inside an eye with an angle in the fold of the flexible circuit cable and a fold between the circuit electrode array and the flexible circuit cable.

FIG. 6 depicts a side view of the prosthesis inside eye 310 with an angle 306 of the flexible circuit cable 12 and a fold 304 between the circuit electrode array 10 and the flexible circuit cable 12. The angle 306 is about 45°-180° and preferably 80°-100°. The fold 306, also called knee, is advantageous because it decreases pressure which would be applied by the flexible circuit cable 10 to the retina 312.

Figure 7:
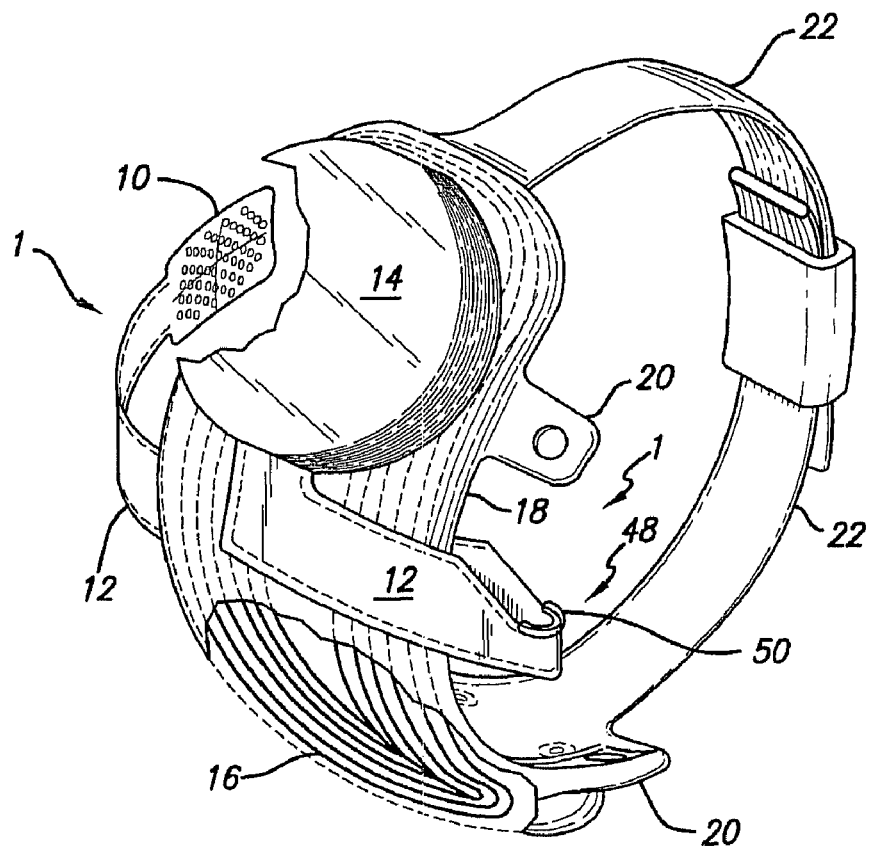
FIG. 7 depicts the implanted portion including a twist in the array to reduce the width of a sclerotomy and a sleeve to promote sealing of the sclerotomy.

FIG. 7 shows the implanted portion of the retinal prosthesis including the additional feature of a gentle twist or fold 48 in the flexible circuit cable 12, where the flexible circuit cable 12 passes through the sclera (sclerotomy). The twist may be a simple sharp twist, or fold 48; or it may be a longer twist, forming a tube. While the tube is rounder, it reduces the flexibility of the flexible circuit. A simple fold 48 reduces the width of the flexible circuit with only minimal impact on flexibility.

Further, silicone or other pliable substance may be used to fill the center of the tube or fold 48 formed by the twisted flexible circuit cable 12. Further it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex or similar material would bond with scleral tissue and promote healing. In particular, a porous material will allow scleral tissue to grow into the pores promoting a good bond.

Alternatively, the flexible circuit electrode array 10 may be inserted through the sclera, behind the retina and placed between the retina and choroid to stimulate the retina subretinally. In this case, it is advantageous to provide a widened portion, or stop, of the flexible circuit cable 12 to limit how far the flexible circuit electrode array is inserted and to limit the transmission of stress through the sclera. The stop may be widening of the flexible circuit 1 or it may be added material such as a bumper or sleeve.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

Figure 8:
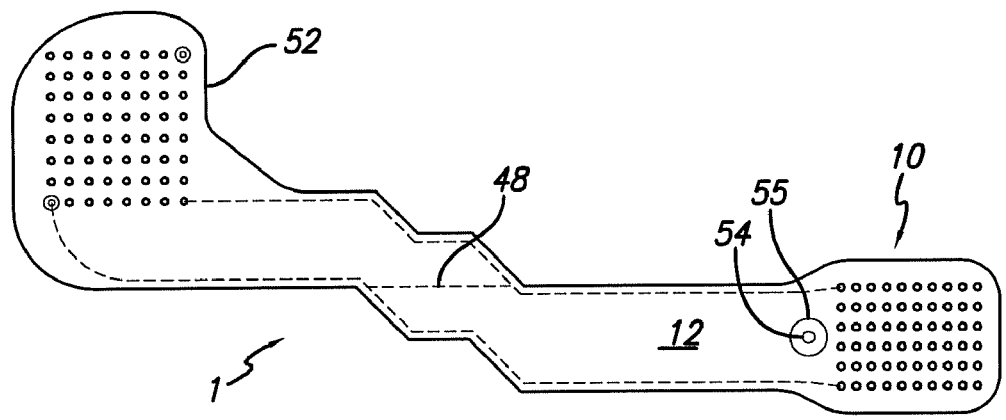
FIG. 8 depicts the flexible circuit array before it is folded and attached to the implanted portion.

FIG. 8 shows the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 9:
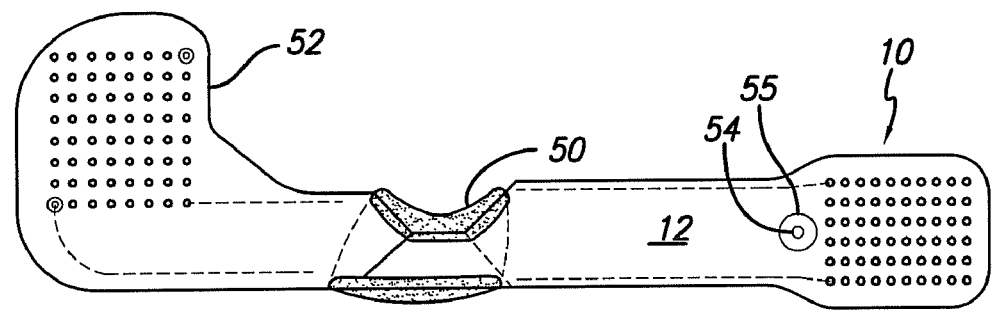
FIG. 9 depicts the flexible circuit array folded.

FIG. 9 shows the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the polymer base layer 70 and the top polymer layer 76. By folding the flexible circuit cable 12 of the flexible circuit electrode array 10, the openings for the bond pad 52 and the electrodes are on the top polymer layer 76 and only the top polymer layer 76 needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture.

An alternative to the bumpers described in FIG. 4, is a skirt of silicone or other pliable material as shown in FIGS. 10, 11, 12, and 13. A skirt 60 covers the flexible circuit electrode array 10, and extends beyond its edges. It is further advantageous to include wings 62 adjacent to the attachment point 54 to spread any stress of attachment over a larger area of the retina. There are several ways of forming and bonding the skirt. The skirt 60 may be directly bonded through surface activation or indirectly bonded using an adhesive.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue.

Figure 11:
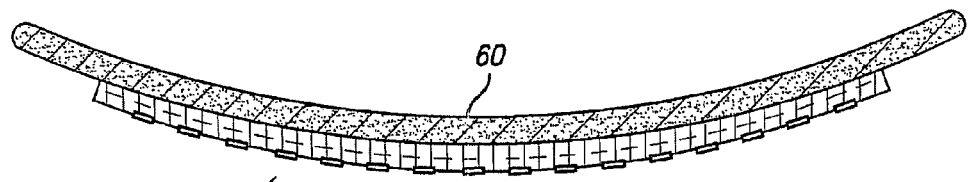
FIG. 11 depicts a flexible circuit array with a protective skirt bonded to the back side of the flexible circuit array.
Figure 12:
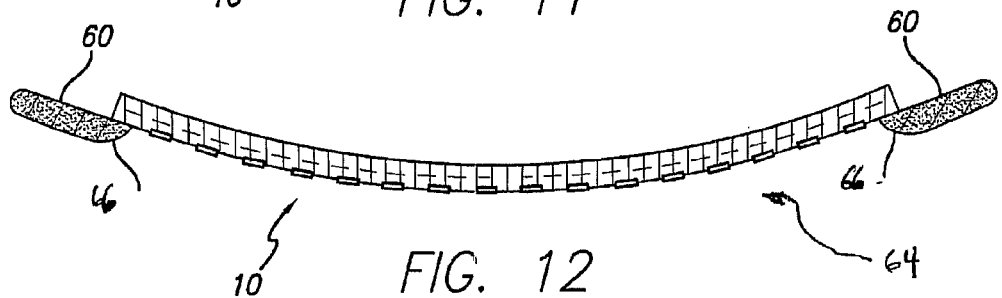
FIG. 12 depicts a flexible circuit array with a protective skirt bonded to the front side of the flexible circuit array.

The simplest solution is to bond the skirt 60 to the back side (away from the retina) of the flexible circuit electrode array 10 as shown in FIG. 11. While this is the simplest mechanical solution, sharp edges of the flexible circuit electrode array 10 may contact the delicate retina tissue. Bonding the skirt to the front side (toward the retina) of the flexible circuit electrode array 10, as shown in FIG. 12, will protect the retina from sharp edges of the flexible circuit electrode array 10. However, a window 64 must be cut in the skirt 60 around the electrodes, producing edge of window 66. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 13:
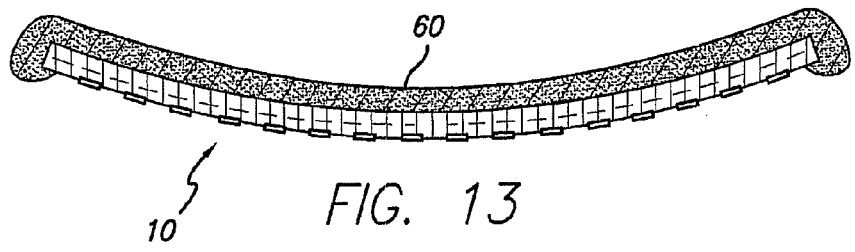
FIG. 13 depicts a flexible circuit array with a protective skirt bonded to the back side of the flexible circuit array and molded around the edges of the flexible circuit array.

FIG. 13 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 14:
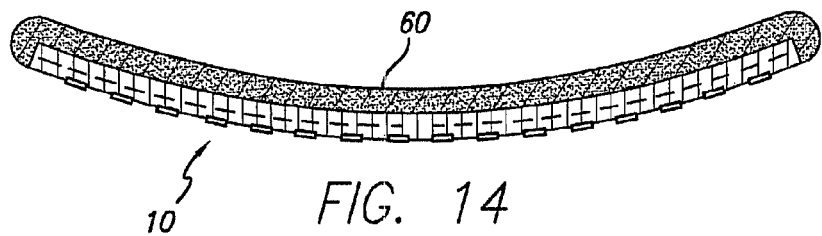
FIG. 14 depicts a flexible circuit array with a protective skirt bonded to the back side of the flexible circuit array and molded around the edges of the flexible circuit array and flush with the front side of the array.

FIG. 14 shows a flexible circuit electrode array 10 similar to FIG. 13, with the skirt 60, flush with the front side of the flexible circuit electrode array 10 rather than extending beyond the front side. While this is more difficult to manufacture, it does not lift the electrodes off the retinal surface as with the array in FIG. 10. It should be noted that FIGS. 11, 13, and 14 show skirt 60 material along the back of the flexible circuit electrode array 10 that is not necessary other than for bonding purposes. If there is sufficient bond with the flexible circuit electrode array 10, it may advantageous to thin or remove portions of the skirt 60 material for weight reduction.

Figure 10:
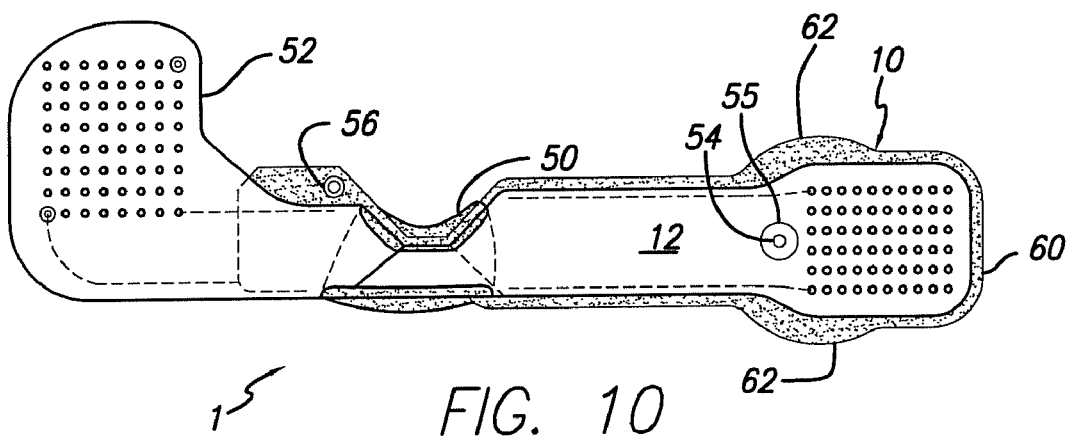
FIG. 10 depicts a flexible circuit array with a protective skirt.
Figure 15:
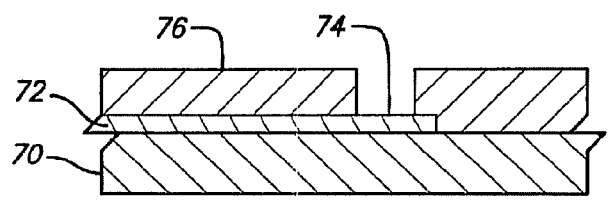
FIG. 15 is an enlarged view of a single electrode within the flexible circuit electrode array.

Referring to FIG. 15, the flexible circuit electrode array 10 is manufactured in layers. A polymer base layer 70 is laid down, commonly by some form of chemical vapor deposition, spinning, meniscus coating or casting. A metal layer 72 (preferably platinum) is applied to the polymer base layer 70 and patterned to create electrodes 74 and traces for those electrodes 74. Patterning is commonly done by photolithographic methods. The electrodes 74 may be built up by electroplating or similar method to increase the surface area of the electrodes 74 and to allow for some reduction in the electrodes 74 over time. Similar plating may also be applied to the bond pads 52 (FIGS. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 16:
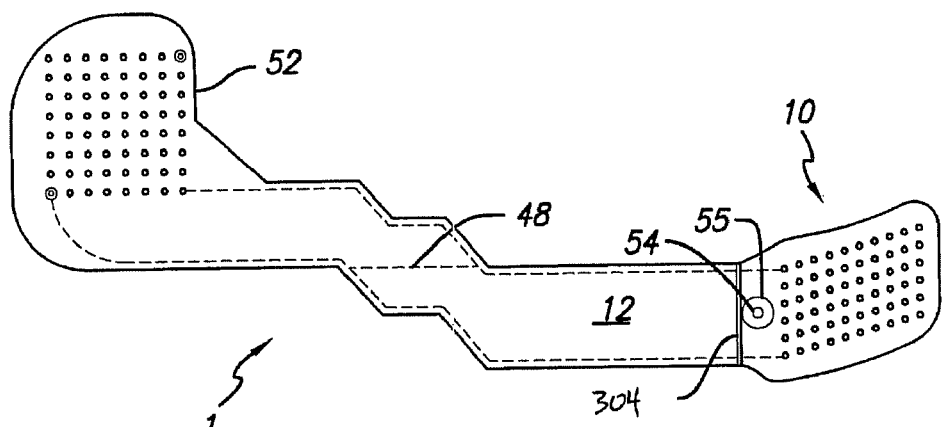
FIG. 16 depicts the flexible circuit array before it is folded and attached to the implanted portion containing an additional fold between the flexible electrode array and the flexible cable.

FIG. 16 depicts the flexible circuit electrode array 10 before it is folded and attached to the implanted portion containing an additional fold 304 between the flexible electrode array 10 and the flexible circuit cable 12. The angle in the fold 304, also called ankle, has an angle of 1°-180°, preferably 80°-120°. The ankle 304 is advantageous in the process of inserting the prostheses in the eye and attaching it to the retina.

Figure 17:
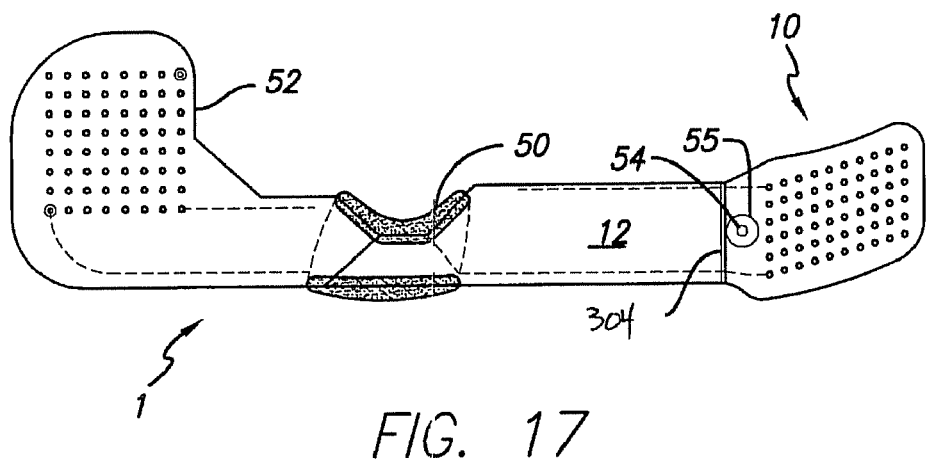
FIG. 17 depicts the flexible circuit array of FIG. 16 folded containing an additional fold between the flexible electrode array and the flexible cable.

FIG. 17 depicts the flexible circuit electrode array 10 FIG. 16 folded containing an additional fold 304 between the flexible electrode array 10 and the flexible circuit cable 12. The flexible circuit electrode array, as shown in FIGS. 8 and 16, differ from each other by the fold 304.

Figure 18:
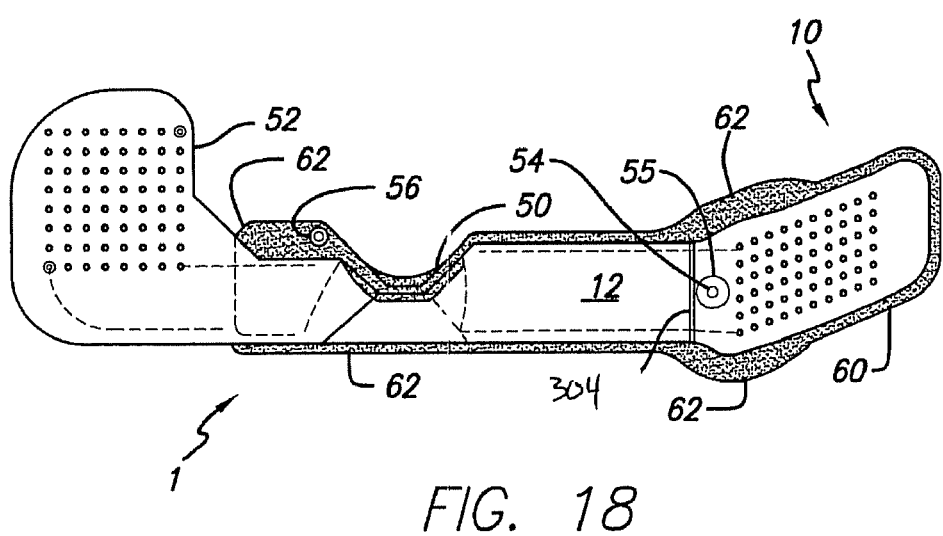
FIG. 18 depicts a flexible circuit array of FIG. 17 with a protective skirt and containing an additional fold between the flexible electrode array and the flexible cable.

FIG. 18 depicts a flexible circuit electrode array of FIG. 17 with a protective skirt 60 and containing an additional fold 304 between the flexible electrode array 10 and the flexible circuit cable 12. The flexible circuit electrode array 10 as shown in FIGS. 10 and 18 differ from each other by the fold 304.

Figure 19:
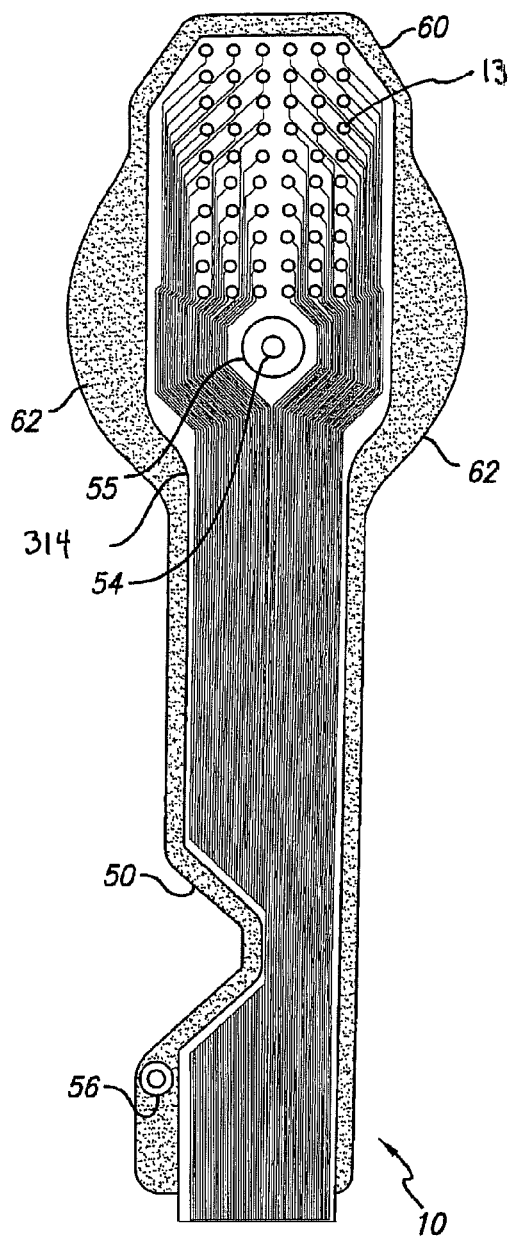
FIG. 19 depicts a top view of a flexible circuit electrode array and flexible circuit cable showing an additional horizontal angle between the flexible circuit electrode array and the flexible circuit cable.

FIG. 19 depicts a top view of a flexible circuit electrode array 10 and flexible circuit cable 12 showing the additional horizontal angle 314 between the flexible circuit electrode array 10 and the flexible circuit cable 12. The angle 314 is from about 1° to about 90° and preferably from about 30° to about 60°.

Figure 20:
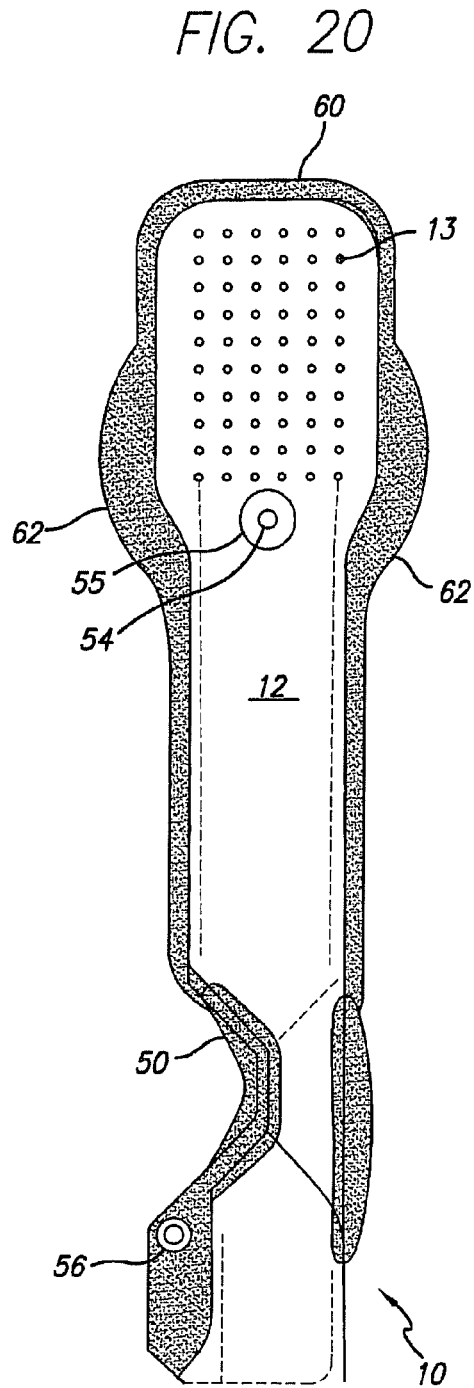
FIG. 20 depicts another variation without the horizontal angle between the flexible circuit electrode array and the flexible circuit cable but with an orientation of the electrodes in the flexible circuit electrode array as shown for the variation in FIG. 19.

FIG. 20 depicts another variation without the horizontal angle 314 between the flexible circuit electrode array 10 and the flexible circuit cable 12 but with an orientation of the electrodes 13 in the flexible circuit electrode array 10, as shown in FIG. 19, for a flexible circuit electrode array 10. The grid of electrodes 13 has the angle 314 with the flexible circuit cable 12 which can be the same as the angle 314 in the flexible circuit electrode array 12 of FIG. 19.

Both variation shown in FIGS. 19 and 20 have the advantage that the electrodes are oriented horizontally if they are inserted into the eye. Further, both variations as shown in FIGS. 19 and 20 can also additionally contain a fold 306.

Figure 21:
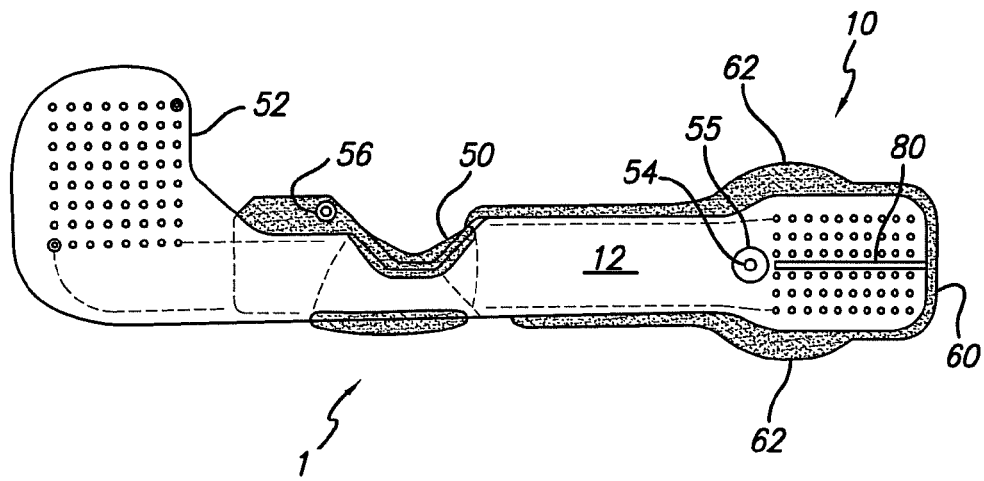
FIG. 21 depicts a top view of a flexible circuit array and flexible circuit cable wherein the array contains a slit along the length axis.

FIG. 21 depicts a top view of a flexible circuit electrode array 10 and flexible circuit cable 12, as shown in FIGS. 10 and 18, wherein the array contains a slit along the longitudinal axis.

Figure 22:
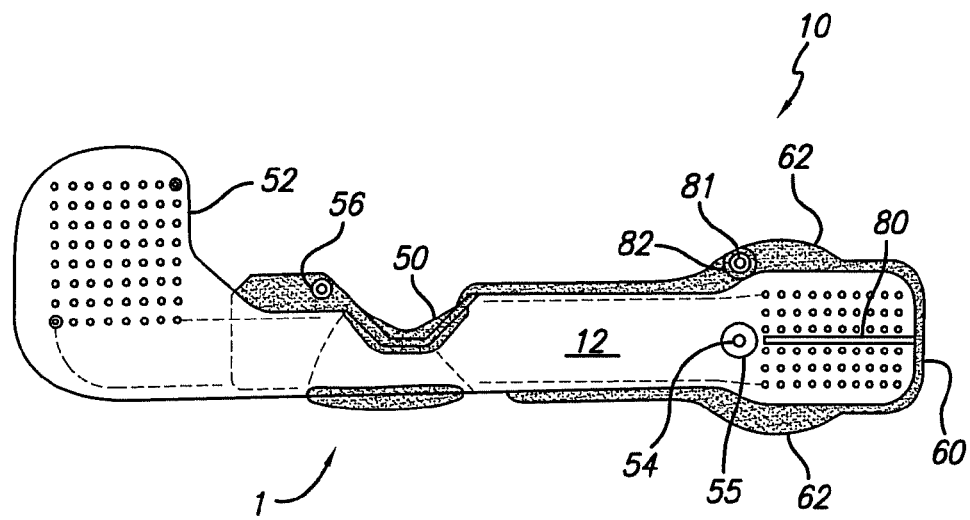
FIG. 22 depicts a top view of a flexible circuit array and flexible circuit cable wherein the array contains a slit along the length axis with a two attachment points.

FIG. 22 depicts a skirt of silicone or other pliable material, as shown in FIGS. 10 to 14. A skirt 60 covers the flexible circuit electrode array 10, and extends beyond its edges. In this embodiment of the present invention the flexible circuit electrode array contains a slit 80 along the longitudinal axis. Further, according to this embodiment, the skirt of silicone or other pliable material contains preferably at least two attachment points 81 and stress reliefs 82 are provided surrounding the attachment points 81. The attachment points 81 are located preferably on the skirt 60 outside the flexible circuit electrode 10 and are positioned as far apart as possible from each other. The two tacks 81 are far enough apart not to cause tenting, therefore fibrosis between the two tacks which cause a traction detachment of the retina. Furthermore, the polyimide is completely between the two tacks, which also reduce the possibility of tenting. Also, this orientation of tacks keeps the tacks away from the axons, which arise from the ganglion cells which are being activated. They are away from the raffe of the retina. The wings act like external tabs or stress relief. The multiple tacks prevent rotation of the array.

The stress relief 82 may be made of a softer polymer than the flexible circuit, or it may include cutouts or thinning of the polymer to reduce the stress transmitted from the retina tack to the flexible circuit electrode array 10.

Figure 23:
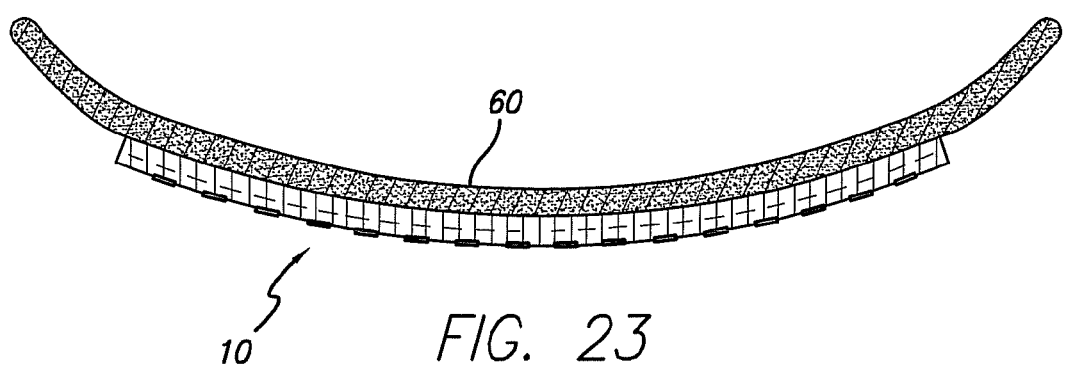
FIG. 23 depicts a flexible circuit array with a protective skirt bonded to the back side of the flexible circuit array with a progressively decreasing radius.

FIG. 23 depicts a flexible circuit electrode array 10 with a protective skirt 60 bonded to the back side of the flexible circuit electrode array 10 with a progressively decreasing radius.

Figure 23A:
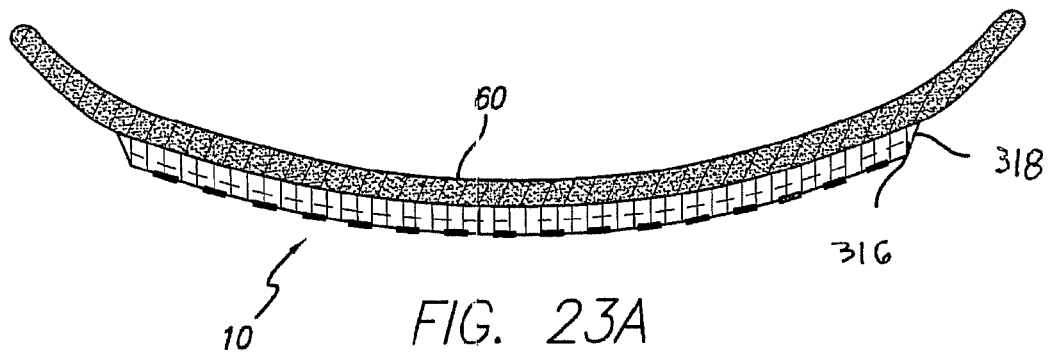
FIG. 23a depicts a variation of a flexible circuit array with a protective skirt bonded to the back side of the flexible circuit array with a progressively decreasing radius.

FIG. 23*a* depicts a flexible circuit electrode array 10 with a protective skirt 60 bonded to the back side of the flexible circuit electrode array 10 with a progressively decreasing radius. This variation shows an angle 316 greater than 90°. This angle is created by laser cutting. The laser cuts the polymer with an angle 316. This leaves a sharp edge 318. To avoid the sharp edge coming into contact with the retina, the polyimide layer is turned around after the laser cutting and attached upside down to the protective skirt 60.

Figure 24:
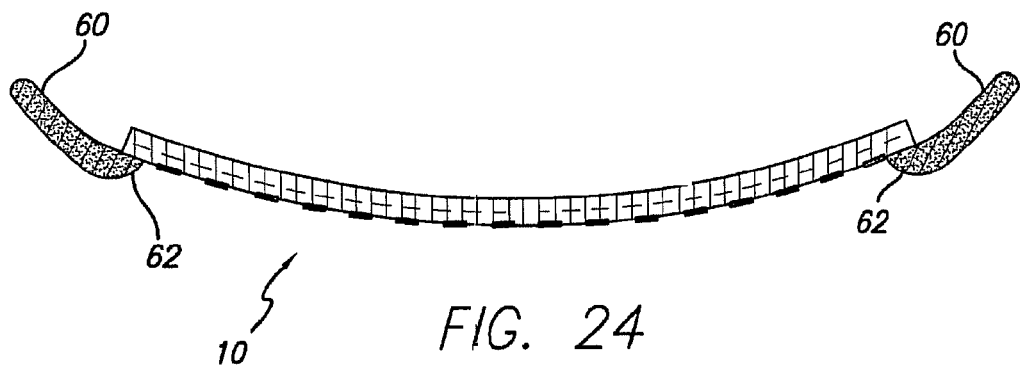
FIG. 24 depicts a flexible circuit array with a protective skirt bonded to the front side of the flexible circuit array with a progressively decreasing radius.

FIG. 24 depicts a flexible circuit electrode array 10 with a protective skirt 60 bonded to the front side of the flexible circuit electrode array 10 with a progressively decreasing radius.

Figure 25:
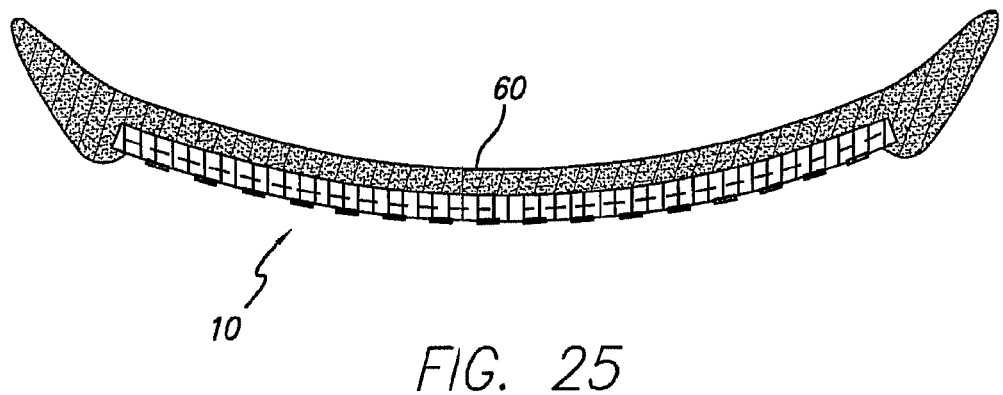
FIG. 25 depicts a flexible circuit array with a protective skirt bonded to the back side of the flexible circuit array and molded around the edges of the flexible circuit array with a progressively decreasing radius.

FIG. 25 depicts a flexible circuit electrode array 10 with a protective skirt 60 bonded to the back side of the flexible circuit electrode array 10 and molded around the edges of the flexible circuit electrode array 10 with a progressively decreasing radius.

Figure 26:
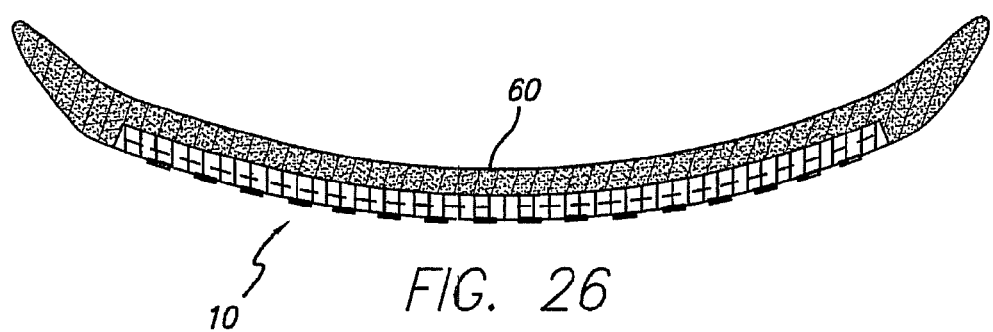
FIG. 26 depicts a flexible circuit array with a protective skirt bonded to the back side of the flexible circuit array and molded around the edges of the flexible circuit array and flush with the front side of the array with a progressively decreasing radius.

FIG. 26 depicts a flexible circuit electrode array 10 with a protective skirt 60 bonded to the back side of the flexible circuit electrode array 10 and molded around the edges of the flexible circuit electrode array 10 and flush with the front side of the flexible circuit electrode array 10 with a progressively decreasing radius.

Figure 27:
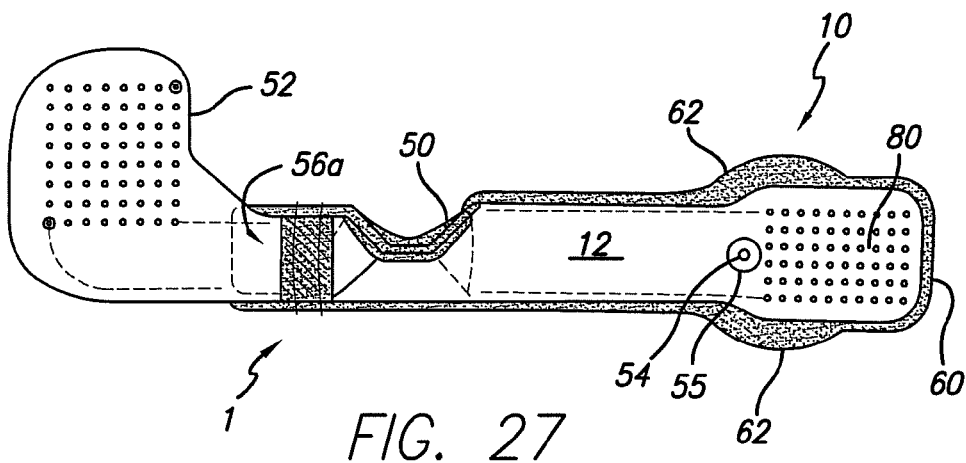
FIG. 27 depicts a side view of the flexible circuit array with a skirt containing a grooved and rippled pad instead a suture tab.
Figure 28:
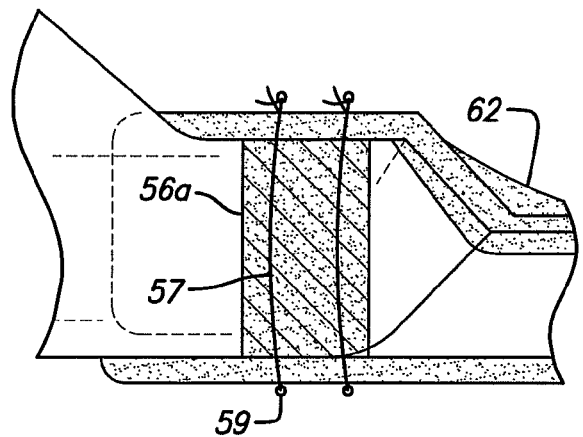
FIG. 28 depicts a side view of the enlarged portion of the skirt shown in FIG. 27 containing a grooved and rippled pad and a mattress suture.

FIG. 27 depicts a side view of the array with a protective skirt 60 containing a grooved and rippled pad 56*a* instead a suture tab 56. This pad 56*a* has the advantage of capturing a mattress suture 57. A mattress suture 57 has the advantage of holding the grove or rippled pad 56*a* in two places as shown in FIG. 28. Each mattress suture 57 is fixed on the tissue in two places 59. A mattress suture 57 on a grooved or rippled mattress 56*a* therefore provides better stability.

Figure 29:
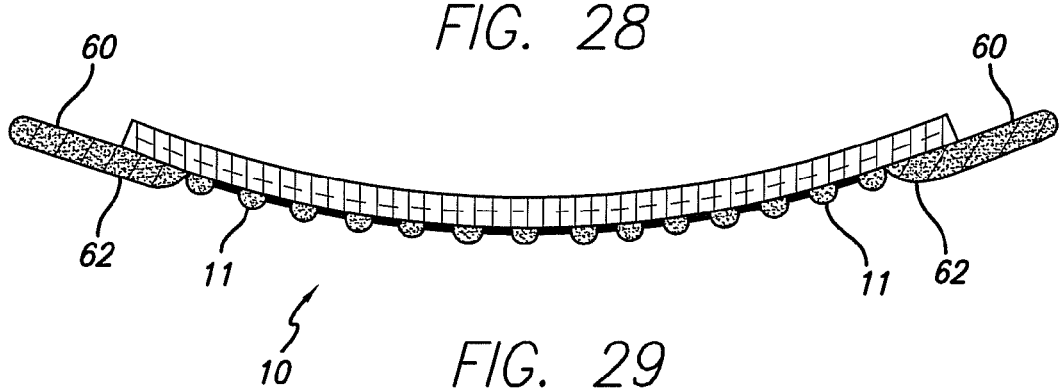
FIG. 29 depicts a flexible circuit array with a protective skirt bonded to the front side of the flexible circuit array with individual electrode windows.

FIG. 29 depicts a flexible circuit electrode array 10 with a protective skirt 60 bonded to the front side of the flexible circuit electrode array 10 with individual electrode 13 windows and with material, preferably silicone between the electrodes 13.

Figure 30:
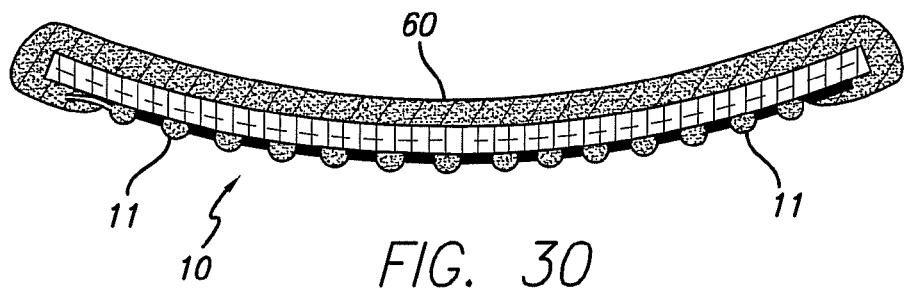
FIG. 30 depicts a flexible circuit array with a protective skirt bonded to the back side of the flexible circuit array and molded around the edges of the flexible circuit array with individual electrode windows.

FIG. 30 depicts a flexible circuit electrode array 10 with a protective skirt bonded to the back side of the flexible circuit electrode array 10 and molded around the edges of the flexible circuit electrode array 10 with individual electrode windows and with material, preferably silicone between the electrodes 13.

Figure 31:
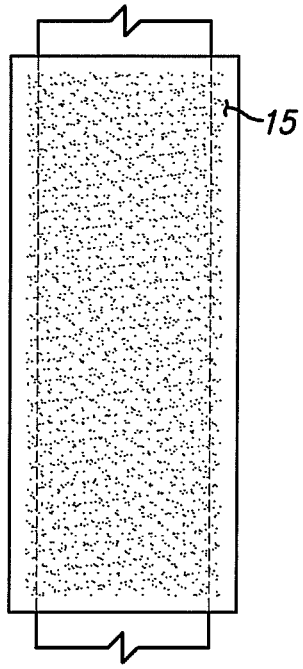
FIGS. 31-36 show several surfaces to be applied on top of the cable.
Figure 32:
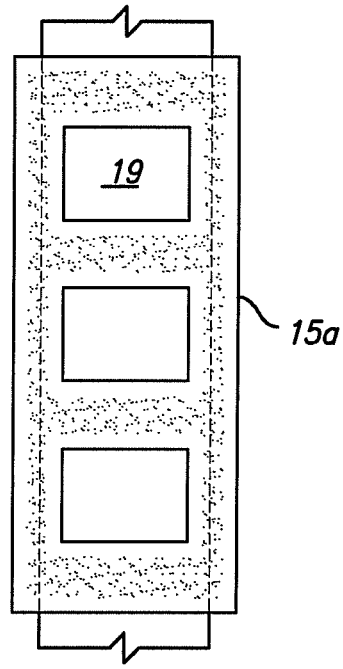
Figure 33:
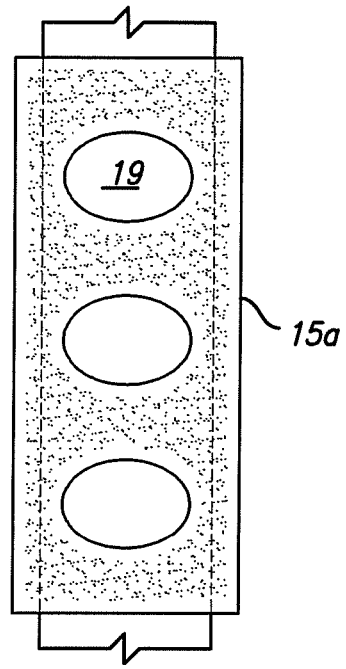
Figure 34:
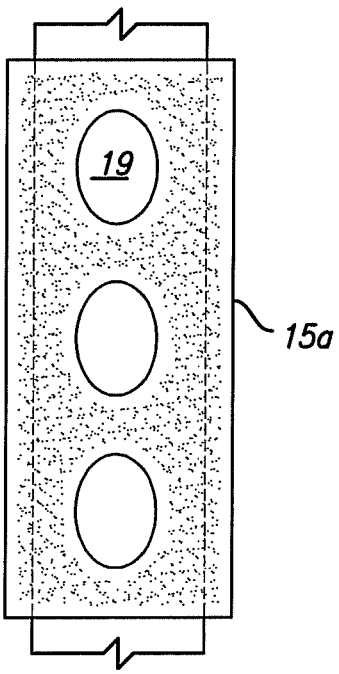
Figure 35:
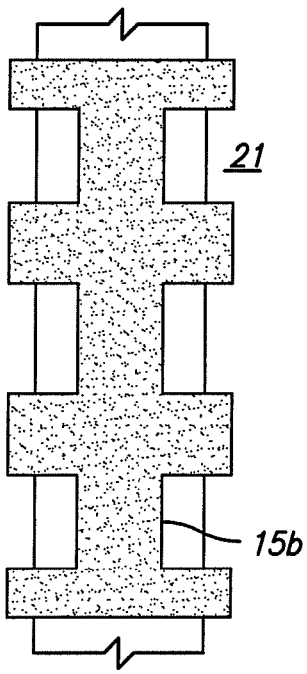
Figure 36:
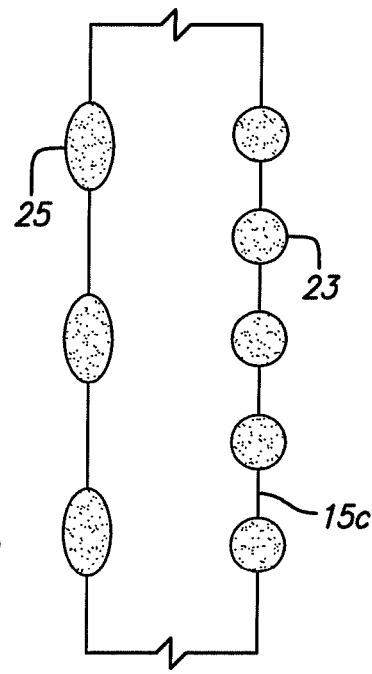

FIGS. 31-36 show several surfaces to be applied on top of the cable. The surfaces are thin films containing a soft polymer, preferably silicone. FIG. 31 shows a flange 15: A flange 15 can be a solid film of material containing silicone added to the surface of the polymer containing polyimide. FIGS. 32-34 show a ladder 15*a*: A ladder 15*a* is a flange with material removed from central portions in some shape 19. FIG. 35 shows a skeleton structure 15*b*. A skeleton 15*b* is a flange with material removed from perimeter portions in some shape 21. FIG. 36 shows a structure 15*c* with beads 23 and bumpers 25. A bead 23 is added to perimeter portions of the polymer cable without material being added on the central area. A bumper 25 can be an extended or continuous version of the beaded approach. Both approaches are helpful in preventing possible injury of the tissue by the polymer.

Figure 37:
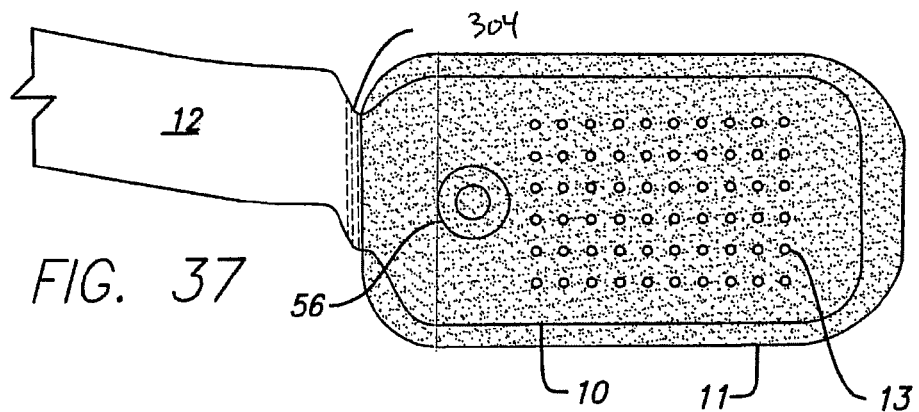
FIG. 37 depicts the top view of the flexible circuit array being enveloped within an insulating material.

FIG. 37 depicts the top view of the flexible circuit electrode array 10 being enveloped within an insulating material 11. The electrode array 10 comprises oval-shaped electrode array body 10, a plurality of electrodes 13 made of a conductive material, such as platinum or one of its alloys, but that can be made of any conductive biocompatible material such as iridium, iridium oxide or titanium nitride. The electrode array 10 is enveloped within an insulating material 11 that is preferably silicone. "Oval-shaped" electrode array body means that the body may approximate either a square or a rectangle shape, but where the corners are rounded. This shape of an electrode array is described in the U.S. Patent Application No. 20020111658, entitled "Implantable retinal electrode array configuration for minimal retinal damage and method of reducing retinal stress" and No. 20020188282, entitled "Implantable drug delivery device" to Robert J. Greenberg, et al., the disclosures of both are incorporated herein by reference.

The material body 11 is made of a soft material that is compatible with the electrode array body 10. In a preferred embodiment the body 11 made of silicone having hardness of about 50 or less on the Shore A scale as measured with a durometer. In an alternate embodiment the hardness is about 25 or less on the Shore A scale as measured with a durometer.

Figure 38:
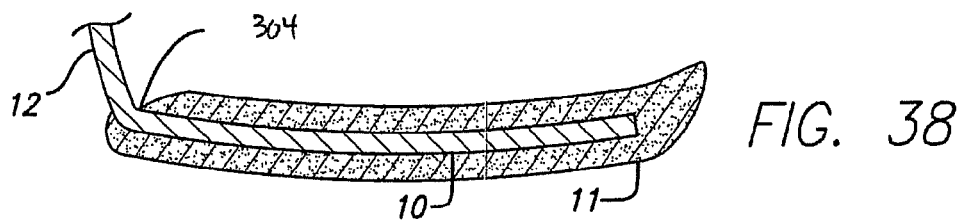
FIG. 38 depicts a cross-sectional view of the flexible circuit array being enveloped within an insulating material.

FIG. 38 depicts a cross-sectional view of the flexible circuit electrode array 10 being enveloped within an insulating material 11. It shows how the edges of the material body 11 lift off due to the contracted radius. The electrode array 10 preferably also contains a fold 304 between the cable 12 and the electrode array 10. The angle of the fold 304 secures a relief of the implanted material.

Figure 39:
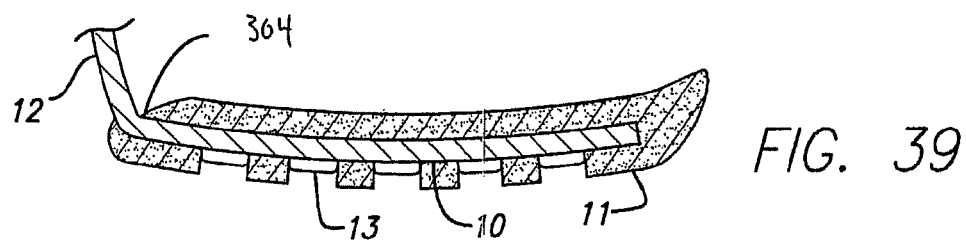
FIG. 39 depicts a cross-sectional view of the flexible circuit array being enveloped within an insulating material with open electrodes and the material between the electrodes.

FIG. 39 depicts a cross-sectional view of the flexible circuit electrode array 10 being enveloped within an insulating material 11 with open electrodes 13 and the insulating material 11 between the electrodes 13. This embodiment also has relief between the flexible circuit electrode array 10 and the retina 312.

Figure 40:
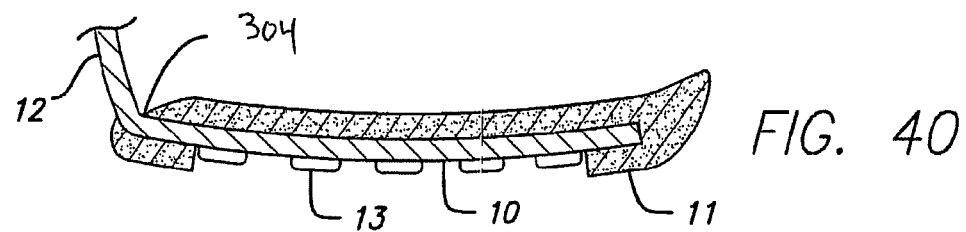
FIG. 40 depicts a cross-sectional view of the flexible circuit array being enveloped within an insulating material with open electrodes.

FIG. 40 depicts a cross-sectional view of the flexible circuit electrode array 10 being enveloped within an insulating material 11 with open electrodes 13. This is another embodiment wherein the electrodes 13 are not separated by the insulating material 11 but the insulating material 11 is extended so that the electrodes 13 are prevented direct contact with the retina 312.

Figure 41:
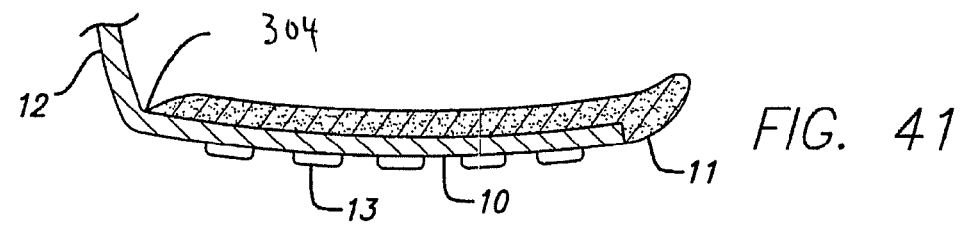
FIG. 41 depicts a cross-sectional view of the flexible circuit array being enveloped within an insulating material with electrodes on the surface of the material.

FIG. 41 depicts a cross-sectional view of the flexible circuit electrode array 10 being enveloped within an insulating material 11 with electrodes 13 on the surface of the material 11. This is a further embodiment with the electrode 13 on the surface of the material 11, preferably silicone. The embodiments, shown in FIGS. 39, 40, and 41, show a preferred body 11 containing silicone with the edges being lift off from the retina due to contracted radius of the silicon body 11.

Figure 42:
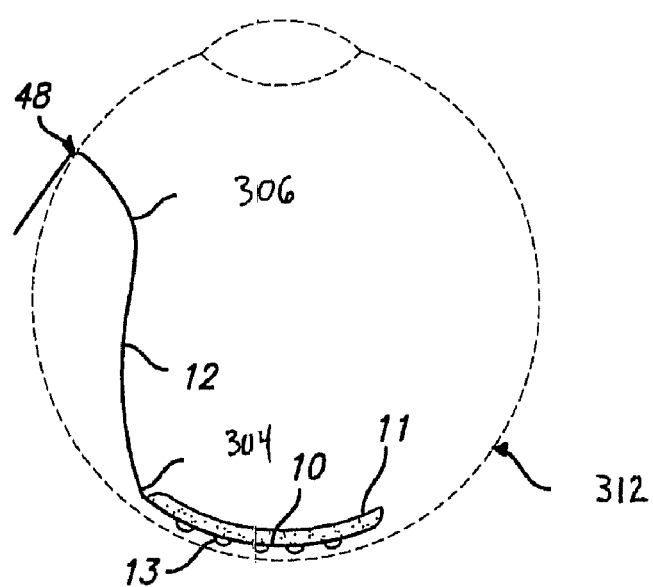
FIG. 42 depicts a cross-sectional view of the flexible circuit array being enveloped within an insulating material with electrodes on the surface of the material insight the eye with an angle in the fold of the flexible circuit cable and a fold between the circuit electrode array and the flexible circuit cable.

FIG. 42 depicts a cross-sectional view of the flexible circuit electrode array 10 being enveloped within an insulating material 11 with electrodes 13 on the surface of the material 11 insight the eye with an angle 306 in the fold of the flexible circuit cable 12 and a fold 304 between the circuit electrode array 10 and the flexible circuit cable 12. The material 11 and electrode array body 10 are in intimate contact with retina 312. The surface of electrode array body 10 in contact with retina 312 is a curved surface with a contracted radius compared to the spherical curvature of retina 312 to minimize stress concentrations therein. Further, the decreasing radius of spherical curvature of material 11 near its edge forms edge relief that causes the edges of the body 11 to lift off the surface of retina 312 eliminating stress concentrations. The edges of body 11 are strongly lifted off due to the contracted radius of the body 11. The edge of body 11 has a rounded edge eliminating stress and cutting of retina 312.

Figure 43:
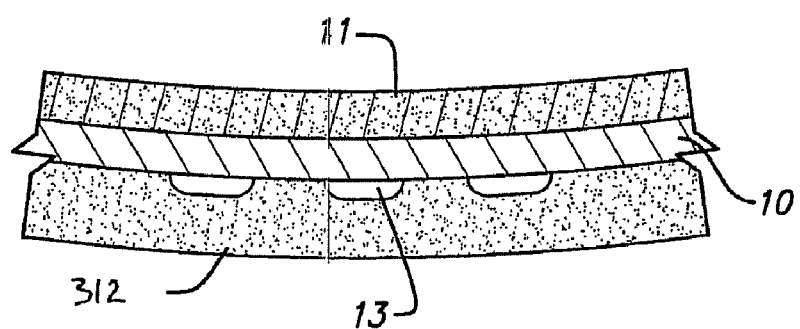
FIG. 43 depicts a side view of the enlarged portion of the flexible circuit array being enveloped within an insulating material with electrodes on the surface of the material insight the eye.

FIG. 43 shows a part of the FIG. 42 enlarged showing the electrode array 10 and the electrodes 13 enveloped by the polymer material, preferably silicone 11 being attached to the retina 312.

The electrode array 10 embedded in or enveloped by the polymer material, preferably silicone 11 can be preferably produced through the following steps. The soft polymer material which contains silicone is molded into the designed shape and partially hardened. The electrode array 10, which preferably contains polyimide, is introduced and positioned in the partially hardened soft polymer containing silicone. Finally, the soft polymer 11 containing silicone is fully hardened in the designed shape enveloping the electrode array 10. The polymer body 11 has a shape with a contracted radius compared with the retina 312 so that the edges of the body 11 lift off from the retina 312.

FIGS. 44-46 show application of the present invention to a cochlear prosthesis. FIG. 44 shows a front view of cochlear electrode array 110. The cochlear electrode array 110 tapers toward the top to fit in an ever smaller cochlea and because less width is required toward the top for metal traces. The electrodes 174 are arranged linearly along the length of the cochlear electrode array 110. Further a skirt 160 of more compliant polymer, such as silicone, surrounds the cochlear electrode array 110. FIG. 45 is a side view of the cochlear electrode array 110. The cochlear electrode array 110 includes a polymer base layer 70, metal trace layer 172 and a top polymer layer 76. Openings in the top polymer layer 76 define electrodes 174.

The cochlear electrode array 110 is made flat as shown if FIGS. 44 and 13B. It is then thermoformed, as described above, into a spiral shape to approximate the shape of the cochlea, as shown in FIG. 46. The cochlear electrode array 110 is implanted with the polymer base layer 70 formed toward the outside of the curvature and with the top polymer layer 76 toward the inside of the curvature. This is opposite of the thermoforming process used for a retinal array. A cortical array would be thermoformed to curve inward like a cochlear array.

FIGS. 47 to 67 depict the sequence of a new process for producing a flexible circuit electrode array. The substrate 322 in that process can be silicon or glass. The polymer can be polyimide, thermoplastic polyimide, silicone, parylene, LCP polymers (Imidex), epoxy resin, PEEK (Victrex), TPE (thermoplastic elastomer) or mixtures thereof. The metals can be titanium, platinum, palladium, iridium, gold, silver, niobium, titanium nitride, iridium oxide, ruthenium, ruthenium oxide, rhodium, or other biocompatible metals or metal alloys or metal layers.

FIG. 47 depicts a cross-sectional view of substrate, comprising glass or silicon. FIG. 48 depicts a cross-sectional view of the substrate and a polymer base layer 70 deposited on the substrate. The polymer can be deposited by spin or dip coating or any other known method. FIG. 49 depicts a cross-sectional view of the substrate with photoresist layer 324 deposited on the polymer. FIG. 50 depicts a cross-sectional view of the layer structure and photoresist layer 324 after being exposed and developed. The developing process includes irradiation of photoresist layer 324 through a template mask and removing the developed parts of the photoresist layer 324. FIG. 51 depicts a cross-sectional view of the layer structure after polymer etching. Polymer can be etched by reactive plasma, reactive-ion etching (RIE), or laser ion milling. FIG. 52 depicts a cross-sectional view of the layer structure after stripping the photoresist layer 324. FIG. 53 depicts a cross-sectional view of the layer structure after depositing thin metal layer 326. FIG. 54 depicts a cross-sectional view of the layer of thin metal layer 326 structure after depositing a photoresist layer 324 on the thin metal layer 326. The metal thin film can contain titanium, platinum, palladium, iridium, gold, silver, niobium, titanium nitride, iridium oxide or other biocompatible metals or metal alloys or metal layers. An adhesion layer 90 containing for example Ti can be applied on top and bottom of the layer of thin metal layer 326. FIG. 55 depicts a cross-sectional view of the layer structure and photoresist layer 324 after being exposed and developed (see for example arrow). FIG. 56 depicts a cross-sectional view of the layer structure after etching the layer of thin metal layer 326 by wet or dry etching (see for example arrow). FIG. 57 depicts a cross-sectional view of the layer structure after stripping the photoresist layer 324. FIG. 58 depicts a cross-sectional view of the layer structure after applying a top polymer layer 76. FIG. 59 depicts a cross-sectional view of the layer structure after applying a photoresist layer 324 on the top polymer layer. FIG. 60 depicts a cross-sectional view of the layer structure and photoresist layer 324 after being exposed and developed (see for example arrow). FIG. 61 depicts a cross-sectional view of the layer structure after etching the top polymer layer 76 (see for example arrow 350). FIG. 62 depicts a cross-sectional view of the layer structure after stripping the photoresist layer 324. FIG. 63 depicts a cross-sectional view of the layer structure after releasing the structure from the substrate. FIG. 64 depicts a cross-sectional view of the layer structure turned upside down and applied on a new substrate 382. FIG. 65 depicts a cross-sectional view of the layer structure after etching down the polymer layer to the metal layer. FIG. 66 depicts a cross-sectional view of the layer structure with deeper etching of the polymer to obtain protruding electrodes. FIG. 67 depicts a cross-sectional view of the layer structure after releasing the structure from the substrate.

Figure 68:
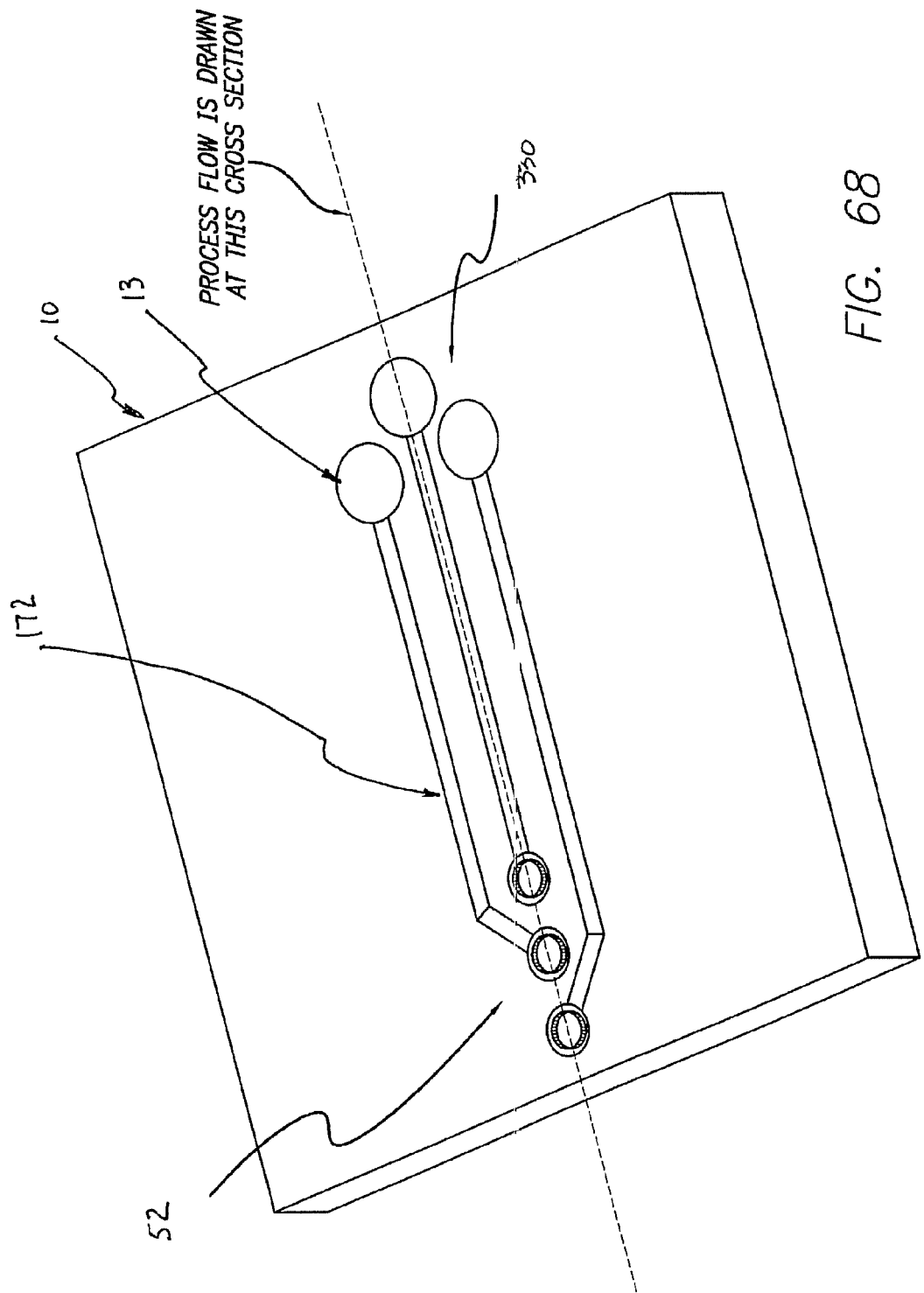
FIG. 68 depicts a top view of a part of the flexible electrode array.

FIG. 68 depicts a top view of part of the flexible circuit electrode array 10.

Figure 69:
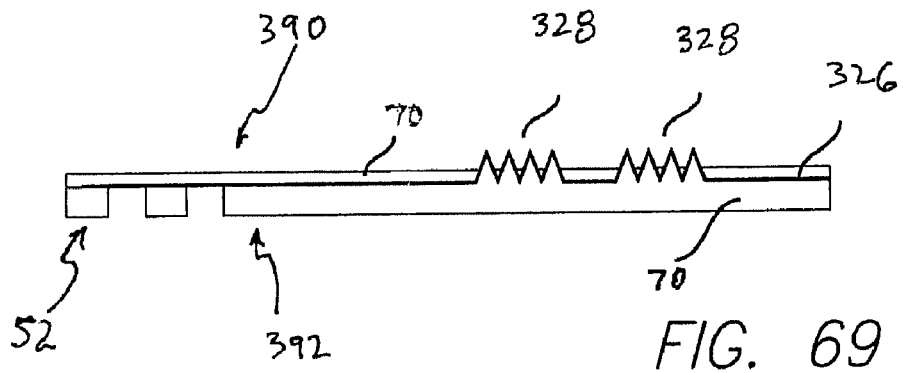
FIG. 69 depicts a cross-sectional view of the layer structure with deeper etching of the polymer to obtain protruding contacts.

FIG. 69 depicts a cross-sectional view of the layer structure with deeper etching of the layer of polymer base layer 70 to obtain protruding electrodes 328. The protruding electrodes have a larger surface and that is an advantage versus flat surface. The flexible circuit electrode array (10) having the plurality of electrodes (74) on a first side (390), further comprising bond pads (52) on a second side (392) of said flexible circuit electrode array (10).

Figure 70:
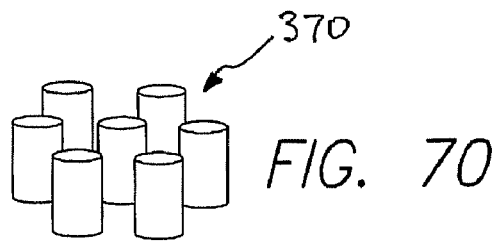
FIG. 70 depicts a top view of a cluster of column shaped electrodes.
Figure 71:
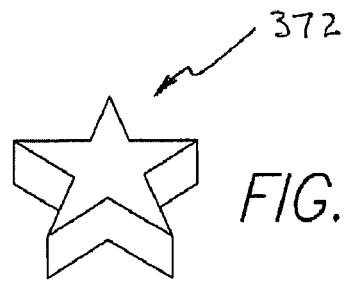
FIG. 71 depicts a top view of a star shaped electrode having a high ratio of parameter length to surface area.
Figure 72:
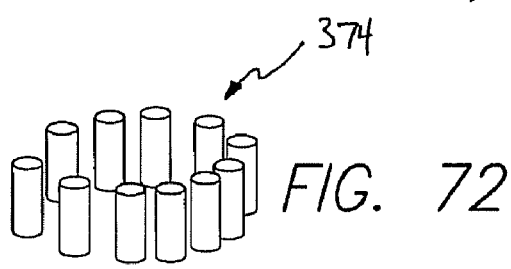
FIG. 72 depicts a top view of a cluster of a column shaped electrode having a high ratio of parameter length to surface area.
Figure 73:
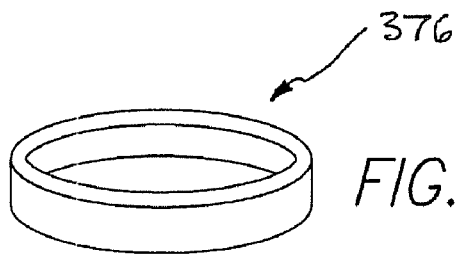
FIG. 73 depicts a top view of an annular shaped electrode.

FIGS. 70 to 73 show other electrode geometries as required to maximize charge uniformity or surface area or contact with tissue, for example to improve stimulus location. Circle shapes, star shapes, square shapes and rings are shown in the electrode array. Each of the shapes can contain overlapping edges and mesh grids. This presents a series of new electrode geometries that control charge transfer characteristics by the strategic use of edges and corners to concentrate current delivery. These designs are an improvement on conventional surface electrode designs which are typically circles. FIG. 70 depicts a top view of a cluster of column shaped electrodes 370. FIG. 71 depicts a top view of a star shaped electrode 372 having a high ratio of parameter length to surface area. FIG. 72 depicts a top view of a cluster of a column shaped electrode 374 having a high ratio of parameter length to surface area. FIG. 73 depicts a top view of an annular shaped electrode 376.

Figure 74:
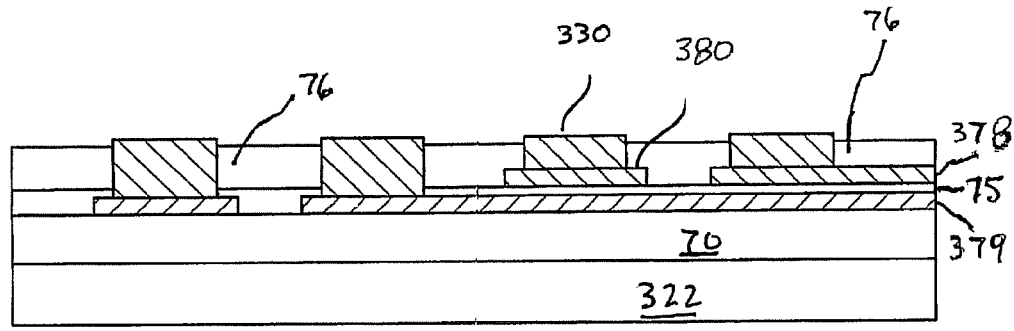
FIG. 74 depicts a cross-sectional view of a multilayer structure.
Figure 75:
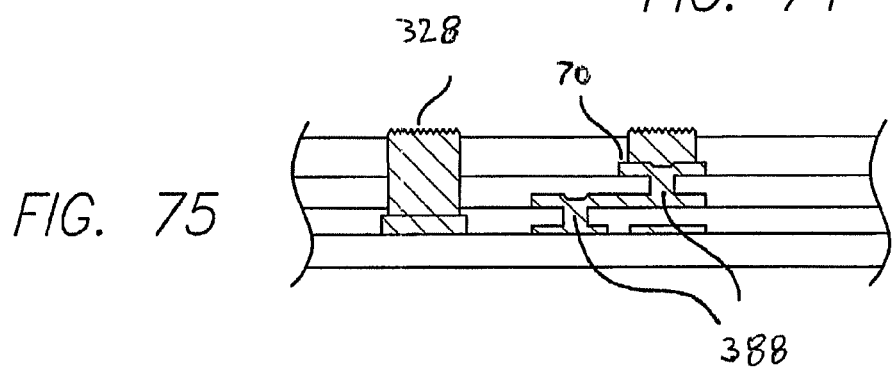
FIG. 75 depicts a cross-sectional view of a multilayer structure with interlayer vias.
Figure 76:
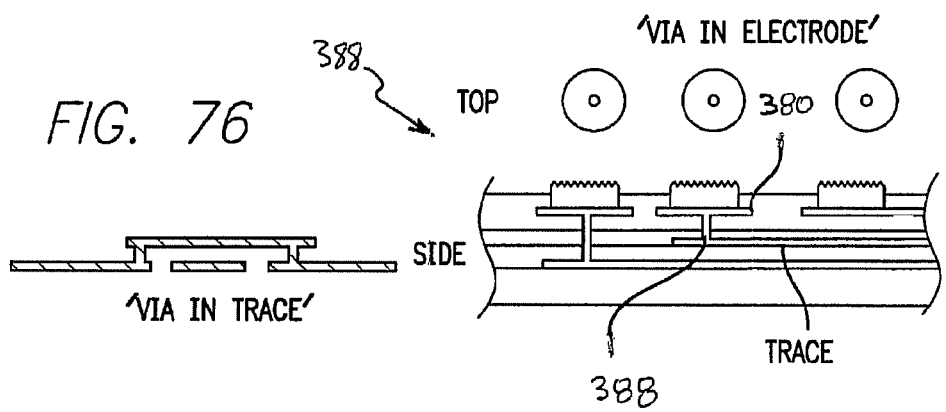
FIG. 76 depicts a cross-sectional view of interlayer vias used to bridge traces.

FIGS. 74 to 76 show a cross-section of multilayer structure. The metal traces are in more than one layer, preferably two or three layers. This variation allows a less broad conducting part of the electrode array. The advantage is that the conducting density is increased. The conducting part can be made thinner by slightly increase of the depth. The increase of the depth has only minor influence on the flexibility of the conducting part. FIG. 76 shows filled via leading into a conducting pad 380. The current enters the electrode through via in the center and not at the edge. If the current is led to the electrode at the edge and the electrode starts to dissolve at the edge to the insulating material it leads to a faster break up of the conductivity. The advantage of the present multilayer is that the conductivity stays stable because even if the electrode starts to dissolve at the edge to the insulating material the conductivity stays stable until the electrode dissolves completely towards the center. Vias can be used to connect traces on different metal layers or to connect an electrode to a metal a trace.

FIG. 74 depicts a cross-sectional view of a multilayer structure. It shows, as an example, two layers of traces 378 and 379. Upper trace 378 has a direct contact with an electrode. Lower trace 379 also has a direct contact to electrode 330.

FIG. 75 depicts a cross-sectional view of a multilayer structure with interlayer vias 388. Vias allow connections between multiple conductor layer, here metal traces. FIG. 75 shows a via that passes electric current through the center of the electrode and not from the edge of the electrode. This has an advantage because the edge of the electrode has a tendency to dissolve faster.

Figure 76A:
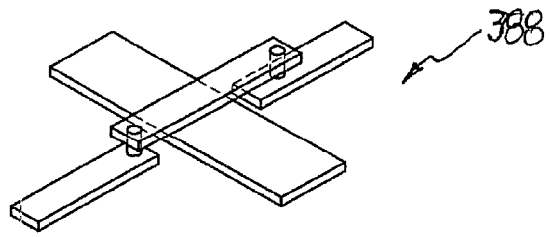
FIG. 76A depicts a top view of interlayer vias used to bridge traces.

FIG. 76 depicts a cross-sectional view of interlayer vias 388 used to bridge traces containing via 388 in the trace. FIG. 76A depicts a top view of interlayer vias 388 used to bridge traces.

This process could be easily adapted to a multi-metal layer electrode array or similar metal and polymer structures that need to have metal electrodes or openings on both sides of the structure.

The invention claimed is:

1. A flexible circuit electrode array (10), comprising:
   a polymer base layer;
   a first metal trace layer coated with a polymer second layer;
   a second metal trace layer coated with a top polymer layer;
   a plurality of electrodes in electrical communication with said first metal trace layer or said second metal trace layer;
   said plurality of electrodes suitable to stimulate neural tissue;
   said polymer base layer and said first metal trace layer and said second metal trace layer embedded in an oval shaped body having a generally oval shape in the plane of a retina, said oval shaped body curved to conform to a spherical curvature of the retina; and
   said polymer second layer and said top polymer layer patterned to reveal said plurality of electrodes.

2. The flexible circuit electrode array according to claim 1, comprising two or three second metal trace layers, separated by said polymer second layer.

3. The flexible circuit electrode array according to claim 1, comprising interlayer vias through said second metal trace layer and attaching more than one metal trace layer.

4. The flexible circuit electrode array according to claim 1, said polymer second layer defines at least one interlayer via, wherein said interlayer via passes an electric current to said electrodes.

5. The flexible circuit electrode array according to claim 1, wherein said plurality of electrodes have a protruding surface.

6. The flexible circuit electrode array according to claim 1, wherein said plurality of electrodes can be shaped as a circle, star, square, ring or other geometric arrangement.

7. The flexible circuit electrode array according to claim 1, said flexible circuit electrode array having said plurality of electrodes on a first side, further comprising bond pads on a second side of said flexible circuit electrode array.

8. The flexible circuit electrode array according to claim 1, wherein said polymer base layer is comprised of polyimide, thermoplastic polyimide, silicone, parylene, LCP polymers, epoxy resin, PEEK, TPE, or mixtures thereof.

9. The flexible circuit electrode array according to claim 1, wherein said more than one metal trace layers are comprised of titanium, platinum, palladium, iridium, gold, silver, niobium, titanium nitride, iridium oxide, ruthenium, ruthenium oxide, rhodium or other biocompatible metals or metal alloys or metal layers.

10. The flexible circuit electrode array according to claim 9, wherein said first and said second metal trace layers comprise an adhesion layer and a thin metal layer.

11. The flexible circuit electrode array according to claim 10, wherein said adhesion layer contains titanium.

12. The flexible circuit electrode array according to claim 1, wherein said top polymer layer is deposited on said polymer base layer and said metal trace layer; and
   wherein said polymer base layer, said metal trace layer and said top polymer layer are thermoformed in a three dimensional shape.

13. The flexible circuit electrode array (10) according to claim 1, wherein said flexible circuit electrode array comprises a flexible circuit cable and at least one grooved or rippled pad for capturing a mattress suture that restrains said flexible circuit cable.

14. The flexible circuit electrode array according to claim 1, wherein said polymer second layer defines at least one interlayer via, wherein said interlayer via passes an electric current from said first metal trace layer to said second metal trace layer.

15. A flexible circuit electrode array comprising:
   a polymer base layer;
   a first metal trace layer, separated by a polymer second layer, deposited on said polymer base layer, including electrodes suitable to stimulate neural tissue;
   said polymer base layer and said metal trace layer embedded in an oval shaped body having a generally oval shape in the plane of a retina, said oval shaped body being curved to substantially conform to a spherical curvature of the retina; and
   comprising at least three metal trace layers separated by said polymer second layer.

* * * * *